(12) United States Patent
Keenan et al.

(10) Patent No.: US 12,382,192 B2
(45) Date of Patent: Aug. 5, 2025

(54) SYSTEM AND METHOD FOR AUTOFOCUSING OF A CAMERA ASSEMBLY OF A SURGICAL ROBOTIC SYSTEM

(71) Applicant: Vicarious Surgical Inc., Charlestown, MA (US)

(72) Inventors: Justin Keenan, Lexington, MA (US); Sammy Khalifa, Medford, MA (US)

(73) Assignee: Vicarious Surgical Inc., Waltham, MA (US)

( * ) Notice: Subject to any disclaimer, the term of this patent is extended or adjusted under 35 U.S.C. 154(b) by 604 days.

(21) Appl. No.: 17/680,017

(22) Filed: Feb. 24, 2022

(65) Prior Publication Data

US 2022/0272272 A1     Aug. 25, 2022

Related U.S. Application Data

(60) Provisional application No. 63/176,634, filed on Apr. 19, 2021, provisional application No. 63/153,128, filed on Feb. 24, 2021.

(51) Int. Cl.
| | | |
|---|---|---|
| *A61B 34/00* | (2016.01) | |
| *A61B 34/30* | (2016.01) | |
| *A61B 90/00* | (2016.01) | |
| *B25J 9/16* | (2006.01) | |
| *H04N 13/239* | (2018.01) | |

(Continued)

(52) U.S. Cl.
CPC ........... *H04N 23/959* (2023.01); *A61B 34/30* (2016.02); *A61B 90/361* (2016.02); *B25J 9/1697* (2013.01); *H04N 13/239* (2018.05); *H04N 13/296* (2018.05); *H04N 23/66* (2023.01); *A61B 2034/302* (2016.02); *A61B 2090/364* (2016.02)

(58) Field of Classification Search
None
See application file for complete search history.

(56) References Cited

U.S. PATENT DOCUMENTS

| | | | |
|---|---|---|---|
| 10,285,765 B2 | 5/2019 | Sachs et al. | |
| 2006/0258938 A1* | 11/2006 | Hoffman | A61B 5/06 600/424 |

(Continued)

FOREIGN PATENT DOCUMENTS

| | | | | |
|---|---|---|---|---|
| KR | 20140060847 | * | 5/2014 | ............ G06T 7/223 |
| WO | 2019/210322 A1 | | 10/2019 | |

(Continued)

OTHER PUBLICATIONS

International Preliminary Report of Patentability for Application No. PCT/US2022/017649, dated Sep. 1, 2022, 9 pages.

(Continued)

*Primary Examiner* — John R Downey
*Assistant Examiner* — Anant A Gupta
(74) *Attorney, Agent, or Firm* — McCarter & English, LLP

(57) ABSTRACT

A surgical robotic system includes a sensor unit, a controller, and a robotic subsystem. The robotic subsystem is in communication with the sensor unit and the controller. Additionally, the robotic subsystem includes a plurality of robotic arms that each have an end effort at a distal end thereof. The robotic subsystem also includes a camera assembly that has at least two cameras and an autofocus unit that automatically focuses a lens of each of the cameras.

18 Claims, 21 Drawing Sheets

(51) Int. Cl.
*H04N 13/296* (2018.01)
*H04N 23/66* (2023.01)
*H04N 23/959* (2023.01)

(56) References Cited

U.S. PATENT DOCUMENTS

| | | | |
|---|---|---|---|
| 2007/0083098 A1* | 4/2007 | Stern | A61B 34/35 |
| | | | 600/407 |
| 2012/0194729 A1* | 8/2012 | Zahniser | G02B 21/244 |
| | | | 348/E5.024 |
| 2014/0267626 A1 | 9/2014 | Lilagan et al. | |
| 2015/0141755 A1* | 5/2015 | Tesar | A61B 1/051 |
| | | | 600/109 |
| 2015/0173846 A1* | 6/2015 | Schneider | A61B 1/00042 |
| | | | 600/424 |
| 2016/0106305 A1 | 4/2016 | McDowall | |
| 2017/0112368 A1 | 4/2017 | Stern et al. | |
| 2018/0061066 A1 | 3/2018 | Frise et al. | |
| 2018/0176483 A1 | 6/2018 | Knorr et al. | |
| 2019/0076199 A1 | 3/2019 | Kline et al. | |
| 2019/0289174 A1 | 9/2019 | Ishii et al. | |
| 2019/0327394 A1* | 10/2019 | Ramirez Luna | A61B 34/77 |
| 2020/0178795 A1* | 6/2020 | Ishikawa | A61F 9/007 |

FOREIGN PATENT DOCUMENTS

| | | |
|---|---|---|
| WO | 2020/018931 A1 | 1/2020 |
| WO | 2020/263870 A1 | 12/2020 |

OTHER PUBLICATIONS

International Search Report and Written Opinion for Application No. PCT/US2022/017649, dated Apr. 28, 2022, 10 pages.

Afshari et al., Real-time FPGA Implementation of Linear Blending Vision Reconstruction Algorithm Using a Spherical Light Field Camera. IEEE Workshop on Signal Processing Systems. pp. 49-54, (2012).

European Office Action for Application No. 22760385.9, dated Dec. 9, 2024, 9 pages.

* cited by examiner

SYSTEM AND METHOD FOR AUTOFOCUSING OF A CAMERA ASSEMBLY OF A SURGICAL ROBOTIC SYSTEM

CROSS REFERENCE TO RELATED APPLICATION(S)

The present disclosure claims priority to U.S. Provisional Patent Application No. 63/153,128 filed on Feb. 24, 2021, and U.S. Provisional Patent Application No. 63/176,634, filed on Apr. 19, 2021, the entire contents of which are incorporated herein by reference.

BACKGROUND

The present disclosure is directed to minimally invasive surgical devices and associated methods and is more specifically related to robotic surgical systems that are insertable into a patient to perform a selected surgery therein.

Since its inception in the early 1990s, the field of minimally invasive surgery has grown rapidly. While minimally invasive surgery vastly improves patient outcome, this improvement comes at a cost to the surgeon's ability to operate with precision and ease. During laparoscopy, the surgeon must insert laparoscopic instruments through a small incision in the patient's abdominal wall. The nature of tool insertion through the abdominal wall constrains the motion of laparoscopic instruments as laparoscopic instruments cannot move side-to-side without injury to the abdominal wall. Standard laparoscopic instruments are limited to four axes of motion. These four axes of motion are movement of the instrument in and out of the trocar (axis 1), rotation of the instrument within the trocar (axis 2), and angular movement of the trocar in two planes while maintaining the pivot point of the trocar's entry into the abdominal cavity (axes 3 and 4). For over two decades, the majority of minimally invasive surgery has been performed with only these four degrees of motion.

Existing robotic surgical devices attempted to solve many of these problems. Some existing robotic surgical devices replicate non-robotic laparoscopic surgery with additional degrees of freedom at the end of the instrument. However, even with many costly changes to the surgical procedure, existing robotic surgical devices have failed to provide improved patient outcome in the majority of procedures for which they are used. Additionally, existing robotic devices create increased separation between the surgeon and surgical end-effectors. This increased separation causes injuries resulting from the surgeon's misunderstanding of the motion and the force applied by the robotic device. Because the degrees of freedom of many existing robotic devices are unfamiliar to a human operator, surgeons must train extensively on robotic simulators before operating on a patient in order to minimize the likelihood of causing inadvertent injury.

Typical robotic systems an include one or more robotic arms and one or more associated cameras. To control the existing robotic system, a surgeon sits at a console and controls manipulators with his or her hands and feet, thus controlling the cameras and the robotic arms. Additionally, the cameras can remain in a semi-fixed location, and are moved by a combined foot and hand motion from the surgeon. These semi-fixed cameras with limited fields of view result in difficulty visualizing the operating field.

In conventional surgical robotic systems, there are multiple ways to focus the cameras on the intended surgical site. Typically and conventionally, the surgeon needs to adjust the focus using either a manual dial or based on an autofocus feature of the system based solely on image data received from an image sensor in the camera. Typical autofocus mechanisms in the medical field also can employ a phase detection autofocus, time of flight (light reflection), or some other light-based estimation method.

A drawback of these conventional types of systems is that they require the surgeon to pause the surgical procedure and to manually change the focus of the cameras. This creates distractions to the surgeon during the surgical procedure. In systems that employ autofocus technology, the focus or field of view of the cameras oftentimes does not align or cover the actual portion of the surgical site that the surgeon needs to view and requires a larger depth of field. The conventional cameras that employ a larger depth of fields require more light and thus have less total resolvability.

SUMMARY

In the robotic surgical system of the present disclosure, the system employs the position of the cameras of the camera assembly and the position of the graspers or end effectors of the robotic arms to determine the field of view and the focal length or point of the cameras. By using the positional information of the end effectors relative to the camera, the system of the present disclosure can determine the focal length and focal point of the cameras while concomitantly allowing the surgeon to view the portions of the surgical site that are important or that the surgeon wishes to view, without having to rely solely on the image data from the camera. The system thus has more precise focus with less false positives and further has the ability to constantly keep the desired field of view in focus.

According to one embodiment, the present disclosure provides a surgical robotic system that includes a sensor unit, a controller, and a robotic subsystem. The robotic subsystem is in communication with the sensor unit and the controller. In addition, the robotic subsystem includes a plurality of robotic arms each having an end effector at a distal end thereof and a camera assembly having at least two cameras and an autofocus unit configured to automatically focus a lens of each of the at least two cameras. The controller may be configured to calculate a desired focal distance based on statement information of the cameras and the robotic arms that is received from the sensor unit. In response, the autofocus unit may be configured to automatically focus the lens of each of the at least two cameras based on the desired focal distance.

The state information may include a distance from each camera to each end effector of the robotic arms that is within a field of view of a surgeon. Additionally, the state information may include positional information and orientation information of each camera and each end effector. Based on the calculated desired focal distance, the controller may be configured to determine a focus command according to a particular focal depth and transmit the focus command to the autofocus unit. In response, the autofocus unit may be configured to adjust a physical focal distance of each camera to focus the lens of each of the cameras.

Further, the controller may be configured to filter the desired focal distance to reduce rapid changes in focal data. A strength of a filter used for the filtering may be varied based on a magnitude of head motion of a surgeon. A different desired focal distance may also be calculated for each of the cameras. The desired focal distance may further be calculated using a weighted algorithm. Each of the robotic arms may be weighted differently in the weighted algorithm. The weights of each robotic arm are functions based on system parameters.

In particular, each robotic arm may include a plurality of joints. These joints may include a shoulder joint, an elbow joint, and a wrist joint. Accordingly, the system parameters may include a distance from center of each end effector in a field of view of each camera, a state of each end effector, and a position of the elbow joint. In one embodiment, a focus adjustment speed may be increased as each end effector moves outward from a target location and may be decreased as each end effector moves towards the target location.

According to another embodiment, the present disclosure provides a robotic subsystem that includes a plurality of robotic arms each having an end effector at a distal end thereof and a camera assembly. The camera assembly may include at least two cameras, a controller, and an autofocus unit configured to automatically focus a lens of each of the cameras. The controller may be configured to calculate a desired focal distance based on state information of the at least two cameras and the plurality of robotic arms received from a sensor unit. In response, the autofocus unit may be configured to automatically focus the lens of each of the at least two cameras based on the desired focal distance.

A focus adjustment speed is increased as the robotic arms move outward from a target location and is decreased as the robotic arms move inward toward the target location. Additionally, the state information includes at least one of a distance from each camera to each end effector of the plurality of robotic arms that is within a field of view of a surgeon and positional and orientation information of the at least two cameras and each end effector of the plurality of robotic arms

BRIEF DESCRIPTION OF THE DRAWINGS

These and other features and advantages of the present disclosure will be more fully understood by reference to the following detailed description in conjunction with the attached drawings in which like reference numerals refer to like elements throughout the different views. The drawings illustrate principals of the disclosure and, although not to scale, show relative dimensions.

DETAILED DESCRIPTION

Figure 1:
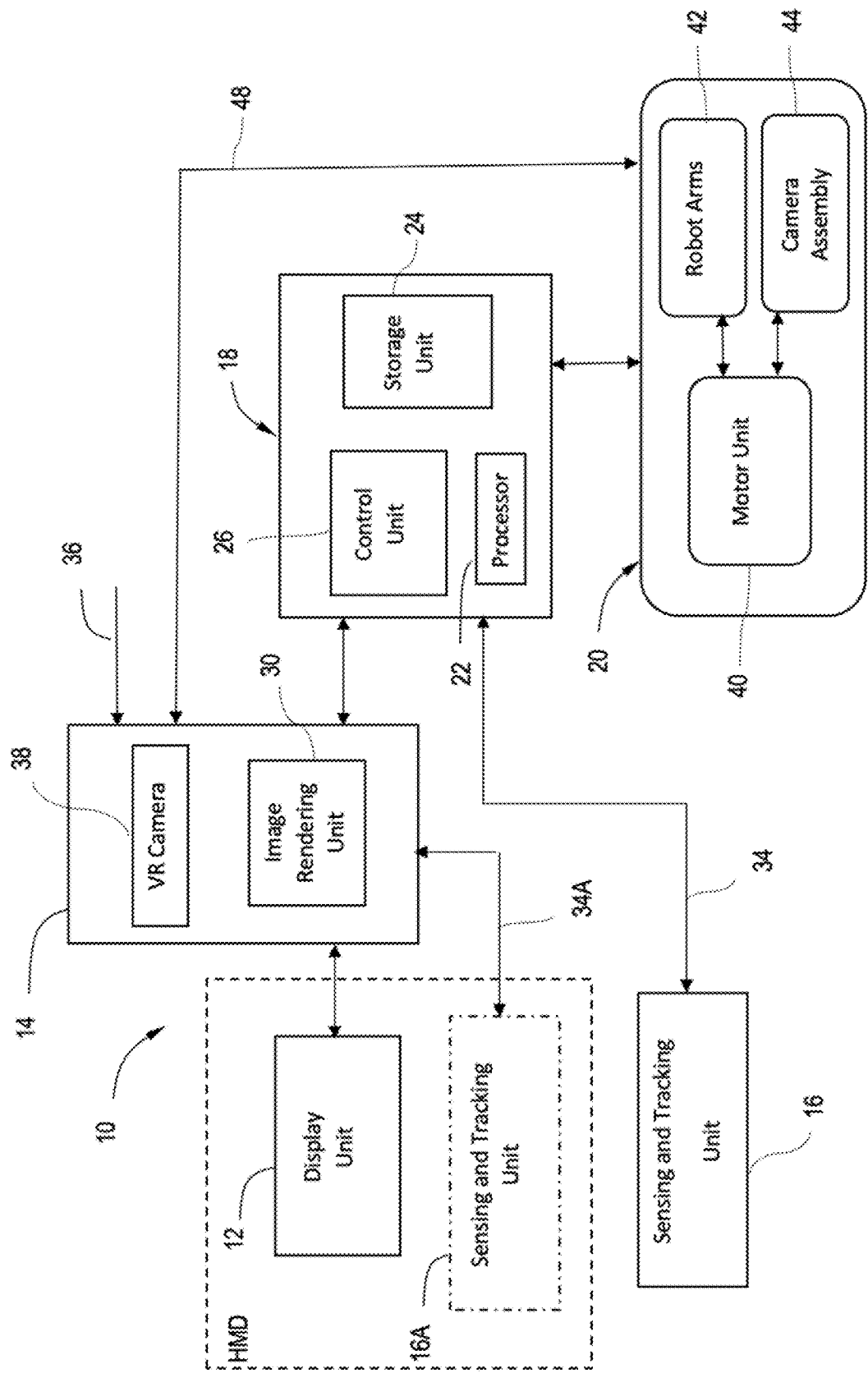
FIG. 1 is a schematic illustration of the surgical robotic system of the present disclosure.

In the following description, numerous specific details are set forth regarding the system and method of the present disclosure and the environment in which the system and method may operate, in order to provide a thorough understanding of the disclosed subject matter. It will be apparent to one skilled in the art, however, that the disclosed subject matter may be practiced without such specific details, and that certain features, which are well known in the art, are not described in detail in order to avoid complication and enhance clarity of the disclosed subject matter. In addition, it will be understood that any examples provided below are merely illustrative and are not to be construed in a limiting manner, and that it is contemplated by the present inventors that other systems, apparatuses, and/or methods can be employed to implement or complement the teachings of the present disclosure and are deemed to be within the scope of the present disclosure.

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor and is specifically programmed to execute the processes described herein. The memory is configured to store the modules and the processor is specifically configured to execute said modules to perform one or more processes which are described further below.

Furthermore, control logic of the present disclosure may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

While the system and method of the present disclosure can be designed for use with one or more surgical robotic systems employed as part of a virtual reality surgery system, the robotic system of the present disclosure may be employed in connection with any type of surgical system, including for example robotic surgical systems, straight-stick type surgical systems, and laparoscopic systems. Additionally, the system of the present disclosure may be used in other non-surgical systems, where a user requires access to a myriad of information, while controlling a device or apparatus.

The system and method disclosed herein can be incorporated and utilized with the robotic surgical device and associated system disclosed for example in U.S. Pat. No. 10,285,765 and in PCT Patent Application No. PCT/US2020/39203, and/or with the camera system disclosed in United States Patent Application Publication No. 2019/0076199, where the content and teachings of all of the foregoing patents, applications and publications are herein incorporated by reference. The surgical robot system that forms part of the present disclosure includes a surgical system having a user workstation, a robot support system (RSS), a motor unit, and an implantable surgical robot subsystem that includes one or more robot arms and one or more camera assemblies. The implantable robot arms and camera assembly can form part of a single support axis robot system or can form part of a split arm architecture robot system.

Figure 3:
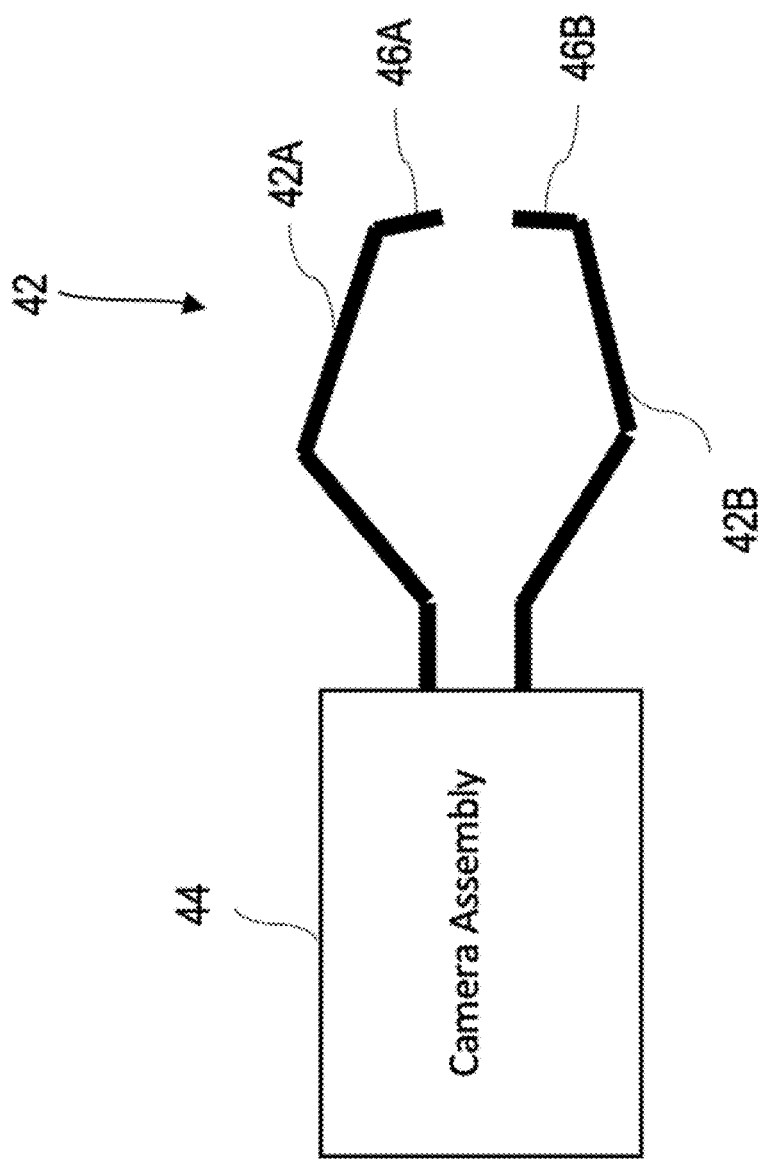
FIG. 3 is a schematic representation of the robotic subsystem of FIG. 1 according to the teachings of the present disclosure.

The robot arms can have joint portions or regions that can be associated with movements associated with the shoulder, elbow, wrist and fingers of the user, as shown for example in FIG. 3 to provide human-like motion. For example, the robotic elbow joint can follow the position and orientation of the human elbow, and the robotic wrist joint can follow the position and orientation of the human wrist. The robot arms can also have associated therewith end regions that can terminate in end-effectors or graspers that follow the movement of one or more of fingers of the user, such as for example the index finger as the user pinches together the index finger and thumb. While the arms of the robot follow movement of the arms of the user, the robot shoulders can be fixed in position. In one embodiment, the position and orientation of the torso of the user is subtracted from the position and orientation of the user's arms. This subtraction allows the user to move his or her torso without the robot arms moving.

FIG. 1 is a schematic block diagram description of a surgical robotic system 10 according to the teachings of the present disclosure. The system 10 includes a display device or unit 12, a virtual reality (VR) computing unit 14, a sensing and tracking unit 16, a computing unit 18, and a robotic subsystem 20. The display unit 12 may be any selected type of display for displaying information, images or video generated by the VR computing unit 14, the computing unit 18, and/or the robotic subsystem 20. The display unit 12 may include or form part of for example a head-mounted display (HMD), a screen or display, a three-dimensional (3D) screen, and the like. The display unit may also include an optional sensor and tracking unit 16A, such as can be found in commercially available head mounted displays. The sensing and tracking units 16 and 16A may include one or more sensors or detectors that are coupled to a user of the system, such as for example a nurse or a surgeon. The sensors may be coupled to the arms of the user and if a head-mounted display is not used, then additional sensors may also be coupled to a head and/or neck region of the user. The sensors in this arrangement are represented by the sensor and tracking unit 16. If the user employs a head-mounted display, then the eyes, head and/or neck sensors and associated tracking technology may be built-in or employed within that device, and hence form part of the optional sensor and tracking unit 16A.

The sensors of the sensor and tracking unit 16 that are coupled to the arms of the surgeon may be preferably coupled to selected regions of the arm, such as for example the shoulder region, the elbow region, the wrist or hand region, and if desired the fingers. The sensors generate position data indicative of the position of the selected portion of the user. The sensing and tracking units 16 and/or 16A may be utilized to control movement of the camera assembly 44 and the robotic arms 42 of the robotic subsystem 20. The position data 34 generated by the sensors of the sensor and tracking unit 16 may be conveyed to the computing unit 18 for processing by a processor 22. The computing unit 20 may be configured to determine or calculate from the position data the position and/or orientation of each portion of the surgeon's arm and convey this data to the robotic subsystem 20.

According to an alternate embodiment, the sensing and tracking unit 16 may employ sensors coupled to the torso of the surgeon or any other body part. Further, the sensing and tracking unit 16 may employ in addition to the sensors an Inertial Momentum Unit (IMU) having for example an accelerometer, gyroscope, magnetometer, and a motion processor. The addition of a magnetometer is standard practice in the field as magnetic heading allows for reduction in sensor drift about the vertical axis. Alternate embodiments also include sensors placed in surgical material such as gloves, surgical scrubs, or a surgical gown. The sensors may be reusable or disposable. Further, sensors may be disposed external of the user, such as at fixed locations in a room, such as an operating room. The external sensors may be configured to generate external data 36 that may be processed by the computing unit and hence employed by the system 10. According to another embodiment, when the display unit 12 is a head mounted device that employs an associated sensor and tracking unit 16A, the device generates tracking and position data 34A that is received and processed by the VR computing unit 14. Further, the sensor and tracking unit 16 may include if desired a hand controller.

In the embodiment where the display is an HMD, the display unit 12 may be a virtual reality head-mounted display, such as for example the Oculus Rift, the Varjo VR-1 or the HTC Vive Pro Eye. The HMD may provide the user with a display that is coupled or mounted to the head of the user, lenses to allow a focused view of the display, and a sensor and/or tracking system 16A to provide position and orientation tracking of the display. The position and orientation sensor system may include for example accelerometers, gyroscopes, magnetometers, motion processors, infrared tracking, eye tracking, computer vision, emission and sensing of alternating magnetic fields, and any other method of tracking at least one of position and orientation, or any combination thereof. As is known, the HMD can provide image data from the camera assembly 44 to the right and left eyes of the surgeon. In order to maintain a virtual reality experience for the surgeon, the sensor system may track the position and orientation of the surgeon's head, and then relay the data to the VR computing unit 14, and if desired to the computing unit 18. The computing unit 18 may further adjust the pan and tilt of the camera assembly 44 of the robot to follow the movement of the user's head.

The sensor or position data 34A generated by the sensors if associated with the HMD, such as for example associated with the display unit 12 and/or tracking unit 16A, may be conveyed to the computing unit 18 either directly or via the VR computing unit 14. Likewise, the tracking and position data 34 generated by the other sensors in the system, such as from the sensing and tracking unit 16 that can be associated with the user's arms and hands, may be conveyed to the computing unit 18. The tracking and position data 34, 34A may be processed by the processor 22 and may be stored for example in the storage unit 24. The tracking and position data 34, 34A may also be used by the control unit 26, which in response may generate control signals for controlling movement of one or more portions of the robotic subsystem 20. The robotic subsystem 20 may include a user workstation, a robot support system (RSS), a motor unit 40, and an implantable surgical robot that includes one or more robot arms 42 and one or more camera assemblies 44. The implantable robot arms and camera assembly may form part of a single support axis robot system, such as that disclosed and described in U.S. Pat. No. 10,285,765 or can form part of a split arm architecture robot system, such as that disclosed and described in PCT patent application no. PCT/US20/39203.

The control signals generated by the control unit 26 may be received by the motor unit 40 of the robotic subsystem 20. The motor unit 40 may include a series of servomotors that are configured for driving separately the robot arms 42 and the cameras assembly 44. The robot arms 42 may be controlled to follow the scaled-down movement or motion of the surgeon's arms as sensed by the associated sensors. The robot arms 42 may have portions or regions that may be associated with movements associated with the shoulder, elbow, and wrist joints as well as the fingers of the user. For example, the robotic elbow joint may follow the position and orientation of the human elbow, and the robotic wrist joint may follow the position and orientation of the human wrist. The robot arms 42 may also have associated therewith end regions that may terminate in end-effectors that follow the movement of one or more of fingers of the user, such as for example the index finger as the user pinches together the index finger and thumb. While the arms of the robot follow movement of the arms of the user, the robot shoulders are fixed in position. In one embodiment, the position and orientation of the torso of the user is subtracted from the position and orientation of the user's arms. This subtraction allows the user to move his or her torso without the robot arms moving.

The robot camera assembly 44 is configured to provide the surgeon with image data 48, such as for example a live video feed of an operation or surgical site, as well as enable a surgeon to actuate and control the cameras forming part of the camera assembly 44. The camera assembly 44 preferably includes a pair of cameras 60A, 60B, the optical axes of which are axially spaced apart by a selected distance, known as the inter-camera distance, to provide a stereoscopic view or image of the surgical site. The surgeon may control the movement of the cameras 60A, 60B either through movement of a head-mounted display or via sensors coupled to the head of the surgeon, or by using a hand controller or sensors tracking the user's head or arm motions, thus enabling the surgeon to obtain a desired view of an operation site in an intuitive and natural manner. The cameras are movable in multiple directions, including for example in the yaw, pitch and roll directions, as is known. The components of the stereoscopic cameras may be configured to provide a user experience that feels natural and comfortable. In some embodiments, the interaxial distance between the cameras may be modified to adjust the depth of the operation site perceived by the user.

According to one embodiment, the camera assembly 44 may be actuated by movement of the surgeon's head. For example, during an operation, if the surgeon wishes to view an object located above the current field of view (FOV), the surgeon looks in the upward direction, which results in the stereoscopic cameras being rotated upward about a pitch axis from the user's perspective. The image or video data 48 generated by the camera assembly 44 may be displayed on the display unit 12. If the display unit 12 is a head-mounted display, the display may include the built-in tracking and sensor system 16A that obtains raw orientation data for the yaw, pitch and roll directions of the HMD as well as positional data in Cartesian space (x, y, z) of the HMD. However, alternative tracking systems may be used to provide supplementary position and orientation tracking data of the display in lieu of or in addition to the built-in tracking system of the HMD. An example of a camera assembly suitable for use with the present disclosure includes the camera assemblies disclosed in U.S. Pat. No. 10,285,765 and U.S. Publication No. 2019/0076199, to the assignee hereof, the contents of which are incorporated herein by reference.

The image data 48 generated by the camera assembly 44 may be conveyed to the virtual reality (VR) computing unit 14 and may be processed by the VR or image rendering unit 30. The image data 48 may include still photographs or image data as well as video data. The VR rendering unit 30 may include suitable hardware and software for processing the image data and then rendering the image data for display by the display unit 12, as is known in the art. Further, the VR rendering unit 30 may combine the image data received from the camera assembly 44 with information associated with the position and orientation of the cameras in the camera assembly, as well as information associated with the position and orientation of the head of the surgeon. With this information, the VR rendering unit 30 may generate an output video or image rendering signal and transmit this signal to the display unit 12. That is, the VR rendering unit 30 renders the position and orientation readings of the hand controllers and the head position of the surgeon for display in the display unit, such as for example in an HMD worn by the surgeon.

The VR computing unit 14 may also include a virtual reality (VR) camera unit 38 for generating one or more virtual reality (VR) cameras for use or emplacement in the VR world that is displayed in the display unit 12. The VR camera unit 38 may generate one or more virtual cameras in a virtual world, and which may be employed by the system 10 to render the images for the head-mounted display. This ensures that the VR camera always renders the same views that the user wearing the head-mounted display sees to a cube map. In one embodiment, a single VR camera may be used and, in another embodiment, separate left and right eye VR cameras may be employed to render onto separate left and right eye cube maps in the display to provide a stereo view. The FOV setting of the VR camera may self-configure itself to the FOV published by the camera assembly 44. In addition to providing a contextual background for the live camera views or image data, the cube map may be used to generate dynamic reflections on virtual objects. This effect allows reflective surfaces on virtual objects to pick up reflections from the cube map, making these objects appear to the user as if they're actually reflecting the real-world environment.

The robot arms 42 may be composed of a plurality of mechanically linked actuation sections or portions forming joints that may be constructed and combined for rotational and/or hinged movement, to emulate different portions of the human arm, such as for example the shoulder region, elbow region, and wrist region of the arm. The actuator sections of the robot arm are constructed to provide cable-driven, rotational movement for example, but within the confines of reasonable rotational limits. The actuator sections are configured to provide maximum torque and speed with minimum size.

Figure 2:
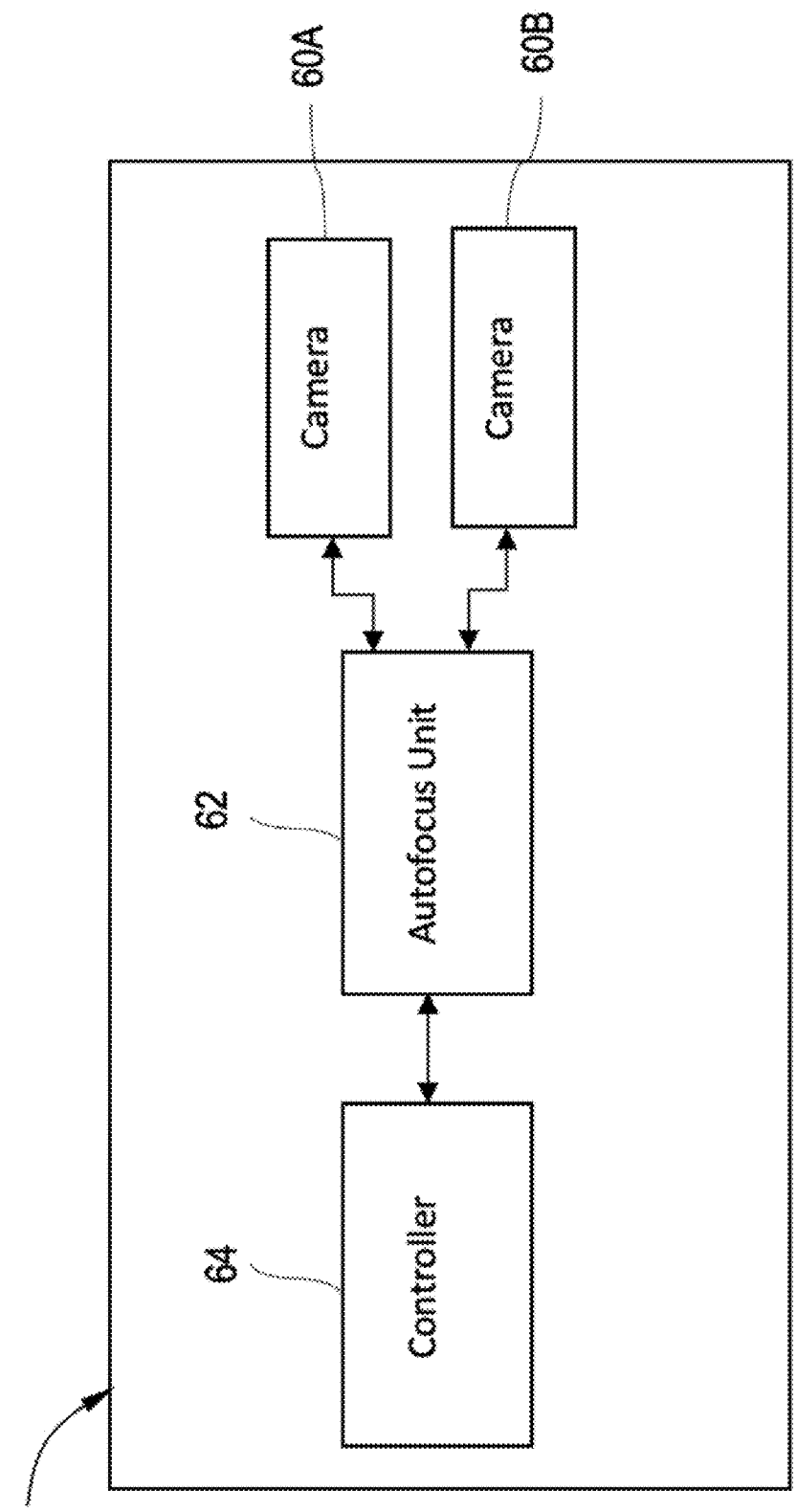
FIG. 2 is a schematic view of the camera assembly of the surgical robotic system of FIG. 1 according to the teachings of the present disclosure.

FIG. 2 is a further detailed view of the camera assembly 44 of the robotic subsystem 20 of the present disclosure. The illustrated camera assembly 44 may include cameras 60A and 60B for providing a stereoscopic view of the surgical site. The cameras may include known elements, including lens and associated optics, image sensors, controllers, and the like. The camera assembly may thus include for example an autofocus unit 62 for automatically focusing the lens of the cameras 60A, 60B. Although shown as a separate unit, the autofocus unit 62 may be included in each camera. The controller 64 may provide control signals for controlling the autofocus unit 62 as well as the cameras 62A, 62B in response to control signals received from the computing unit 18 and/or the motor unit 40.

The illustrated camera assembly 44 exhibits two additional properties that make the autofocus unit 62 more important than other devices on the market. First, the camera assembly 44 has a lot more movement in normal operation which results in the need to focus on different locations more rapidly. Second, the autofocus unit 62 may employ a lens system that utilizes a narrower depth of field than would otherwise be required. As such, the autofocus unit 62 may employ less expensive lens elements, while concomitantly providing better clarity in the focus area.

FIG. 3 is a general schematic representation of the robot arms 42 and the camera assembly 44 of the robotic subsystem 20. The robot arms 42 may include for example separate robot arms 42A and 42B. Each of the robot arms 42A, 42B may include end effectors or graspers 46A, 46B, respectively.

The controller 64 may use or employ positional information received from the motor unit 40 and from any sensors associated with the system, such as for example from the sensor and tracking units 16, 16A and may calculate or determine the desired focal distance. In one embodiment the information utilized is the distance from the camera to each end effector portion 46A, 46B of the robot arms 42A, 42B that are currently in the field of view of the surgeon. The controller 64 may also store a focus curve of each camera 60A, 60B that is calibrated at the factory in distance space and the focal point of each camera may be adjusted by the autofocus unit 62 to be consistent with the location of what the surgeon is looking at using the robot arms 42 as a minimum position in the depth of field in the intended view. As the system 10 moves the robot arms 42 or the camera assembly 44, the focal point of the cameras 60A, 60B may be adjusted accordingly.

Figure 4:
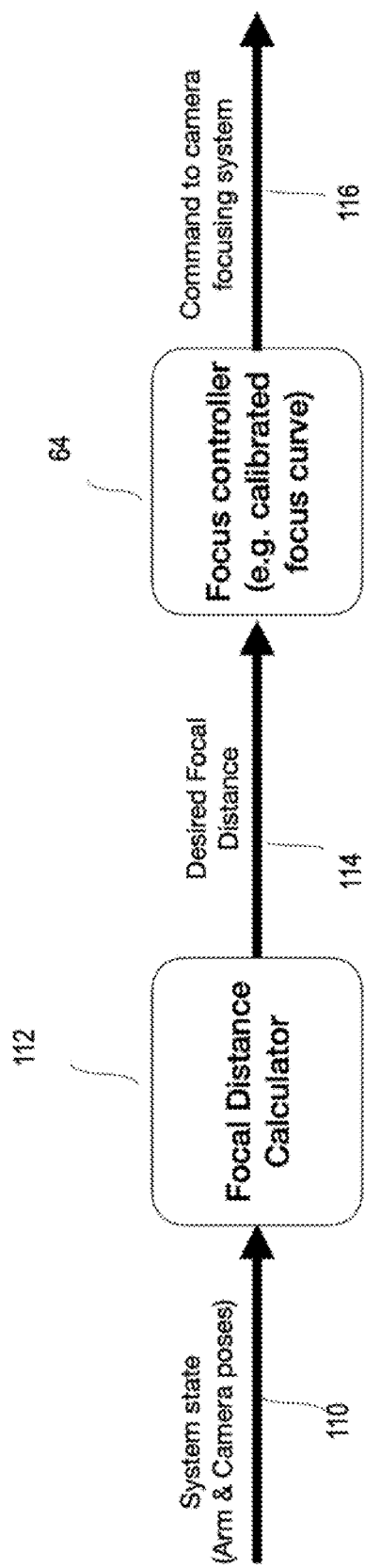
FIG. 4 is a schematic representation illustrating the processing of system state data by a weighted algorithm unit employed by the system of the present disclosure.

As shown in FIG. 4, the desired focal distance may be determined by determining the system state 110 (e.g., arm position and camera position) and then using a selected weighted algorithm 112 to process the system state data 110. The weighted algorithm technique 112 may be configured to match the surgeon's region of interest with a high degree of fidelity and then to focus the camera 40A, 40B on the region with the autofocus unit 62 without direct knowledge of the scene or direct input from the surgeon. The weighted algorithm may determine the desired focal distance 114. The desired focal distance 114 may be transmitted to the controller 64 that may then utilize a variety of methods, including using a calibrated focus curve 100 to determine a selected focus command 116 for the given desired focal depth. The focus command 116 is sent to the autofocus unit 62 to change the physical focal distance of the camera. The weighted algorithm and associated processing may occur in the computing unit 18. Alternatively, the computations may occur in the camera controller 64.

Figure 5A:
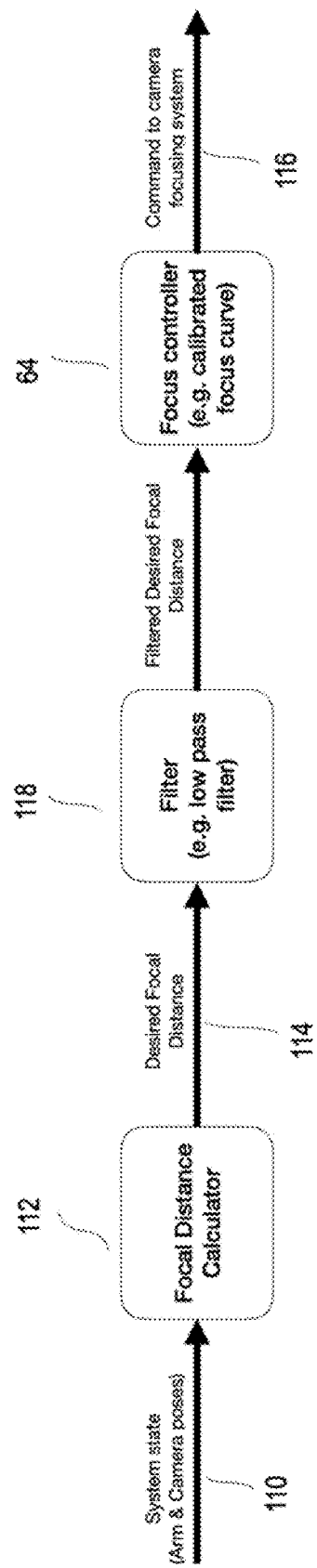
FIGS. 5A-5B are schematic representations illustrating the processing of system state data by a weighted algorithm unit employed by the surgical robotic system according to a second embodiment of the present disclosure.
Figure 5B:
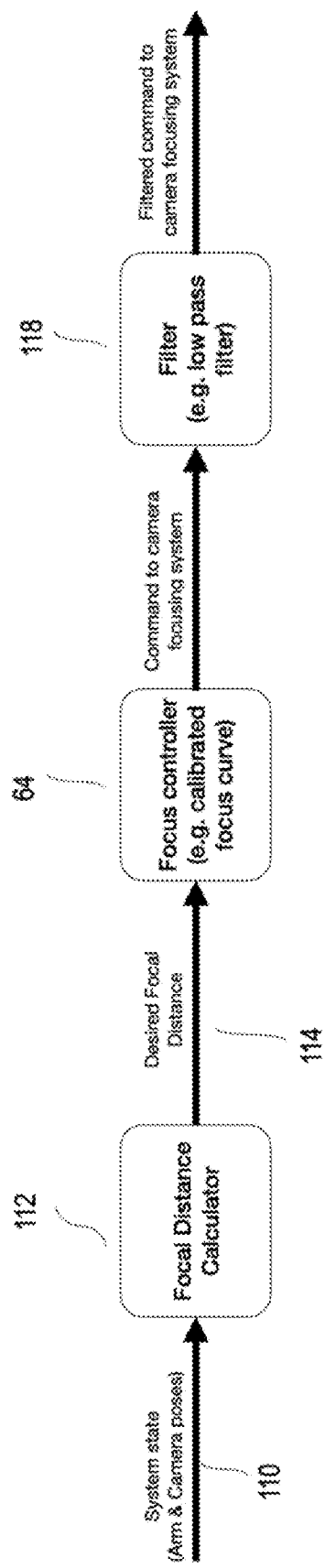

According to an alternate embodiment, the surgical robotic system 10 may employ a filter to process the desired focal distance 114. As shown for example in FIG. 5A, the system via the computing unit 18 may employ the weighted algorithm technique 112 to generate the desired focal distance 114. The desired focal distance 114 may then be passed through an optional filter, such as a low pass filter 118 to reduce large or fast changes in the focal data. The strength of the low pass filter 118 may be adjusted or varied by the magnitude of the head motion (i.e., more head motion results in a less strong filter). The output of the low pass filter 118 may be conveyed to the controller 64. Alternatively, the filter may be positioned at the output of the autofocus unit 62, as shown in FIG. 5B. Notably, the filter is not limited to a low-pass filter and the present disclosure contemplates other known filters.

According to another practice of the present disclosure, the desired focal distance 114 may vary between the cameras 60A, 60B. By having the cameras 60A, 60B focused at positions (e.g., one camera closer and the other camera farther away) from the desired focal distance 114, a composite image may be created with a larger depth of field when the images from the cameras are superimposed.

The system may determine the desired focal distance by taking in the distance between the end effector portions of the robot arms and the cameras and by employing selected weighted values associated with each robot arm. By mathematically combining the weighted values in a selected manner, the controller 64 may determine therefrom the desired focal distance 114. The position and orientation of the camera assembly 44 relative to each end effector 46A, 46B may be determined by the controller 64 of the camera assembly, as well as by the control unit 26. The controller 64 then generates control signals that are received by the autofocus unit 62. In response, the autofocus unit 62 generates signals for varying, adjusting or controlling the focal point or length of the cameras 60A according to known techniques. As the distance between the end effectors and the camera assembly changes, the autofocus unit 62 may automatically adjust the focal point or length of the cameras in response thereto.

Figure 6A:
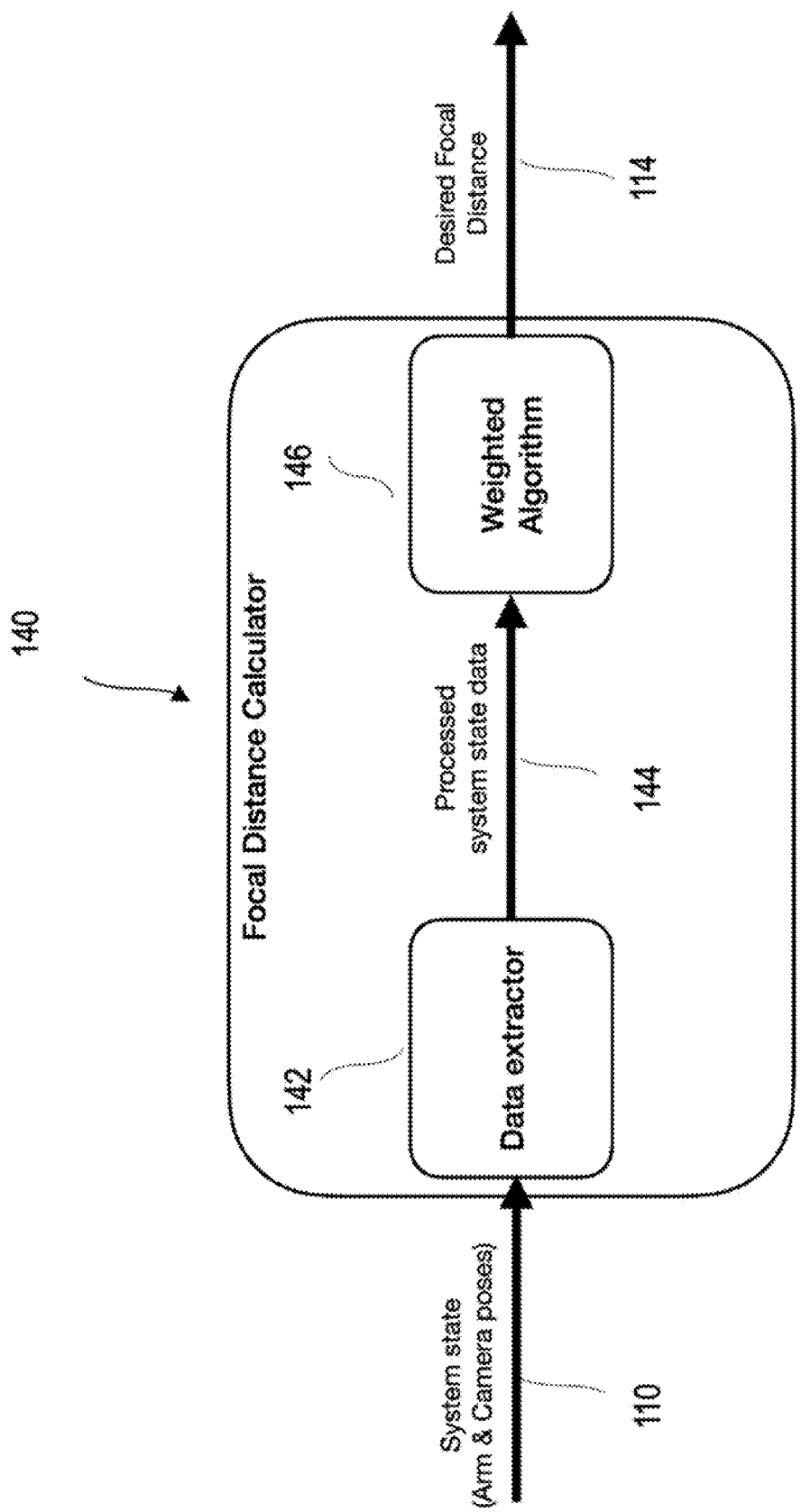
FIG. 6A is a schematic representation illustrating the processing of system state data by a focal distance calculator unit employed by the surgical robotic system according to the teachings of the present disclosure.
Figure 6B:
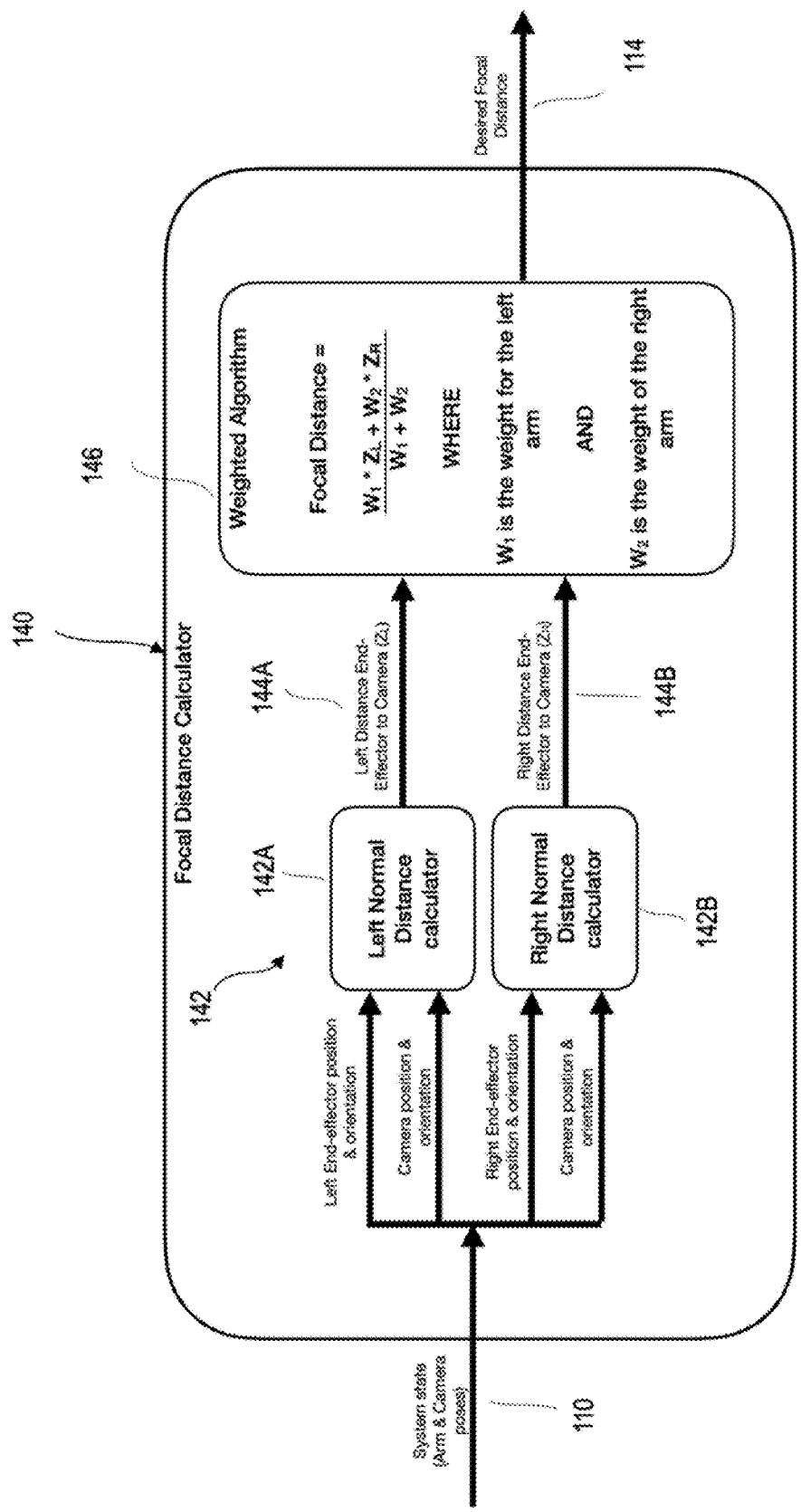
FIG. 6B is a schematic representation illustrating the processing of system state data by a second embodiment of the focal distance calculator unit employed by the surgical robotic system according to the teachings of the present disclosure.

According to one embodiment, the system state data is processed by a weighted algorithm unit to adjust the relative effect that inputs have on the output of the system 10. As shown for example in FIGS. 6A and 6B, system state data 110 defining the state of the positions (e.g., poses) of the robot arms and cameras is generated by the control unit 26. The system state data 110 is then introduced to a focal distance calculator 140 for determining the desired focal distance 114. The focal distance calculator 140 may form part of the computing unit 18 or may form part of the robotic subsystem 20. The focal distance calculator 140 may include a data extractor unit 142 for extracting selected types of data and for generating processed system state data 144. The processed system state data 144 is conveyed to a weighted algorithm unit 146 for applying a weighted algorithm technique to the system state data 144. The weighted algorithm unit 146 generates from the system state data the desired focal distance 114. More specifically, the data extractor unit 142 may employ multiple different distance calculation units for calculating a normal distance of the camera to each robot arm, including for example a left normal distance calculator unit 142A and right normal distance calculator unit 142B. For example, the system state information 110 may include left end effector position and orientation information and left camera position and orientation information that is introduced to the left normal distance calculator unit 142A.

Further, the system state information 110 may include right end effector position and orientation information and right camera position and orientation information that is introduced to the right normal distance calculator unit 142A. The left normal distance calculator unit 142A calculates from the input data left distance data 144A that is indicative of the distance between the left camera and the left end effector. Similarly, the right normal distance calculator unit 142B calculates from the corresponding input data right distance data 144B that is indicative of the distance between right camera and the right end effector. The distance data 144A, 144B is then introduced to the weighted algorithm unit 146 for further processing. The weighted algorithm unit 146 may include a focal distance calculation unit that determines the desired focal distance 114 using the following formula:

$$\text{Focal Distance} = (W_1 * Z_L + W_2 * Z_R)/(W_1 + W_2)$$

where $W_1$ and $W_2$ are representative of selected weighted values associated with the left robot arm and right robot arm, respectively, and $Z_1$ is representative of the distance value 144A from the left normal distance calculation unit 142A and $Z_2$ is representative of the distance value 144B from the right normal distance calculation unit 142B.

As such, according to the weighted algorithm technique, each robot arm is weighted separately and then the values are normalized by dividing by the sum of their weights so that the calculated desired focal distance 114 is within an appropriate range. According to one embodiment of the weighted algorithm technique, both weights $W_1$ and $W_2$ are fixed and equal to one such that the weighted algorithm effectively computes the average of the two distances. According to another embodiment of the weighted algorithm technique, the weights $W_1$ and $W_2$ of the two robot arms may be varied such that one arm becomes more influential relative to the other in determining the desired focal distance 114. In still another embodiment of the weighted algorithm technique, the weights of the two robot arms may be functions (i.e., not fixed) based upon other system parameters. The system parameters may include, for example, how centered an end-effector is in the field of view (FOV) of the camera, the end effector state (i.e., grasper is open, closed or somewhere in between), the position of the elbow joint, or any other parameter that the system may measure and relay to the focal distance calculator unit 140.

Figure 6C:
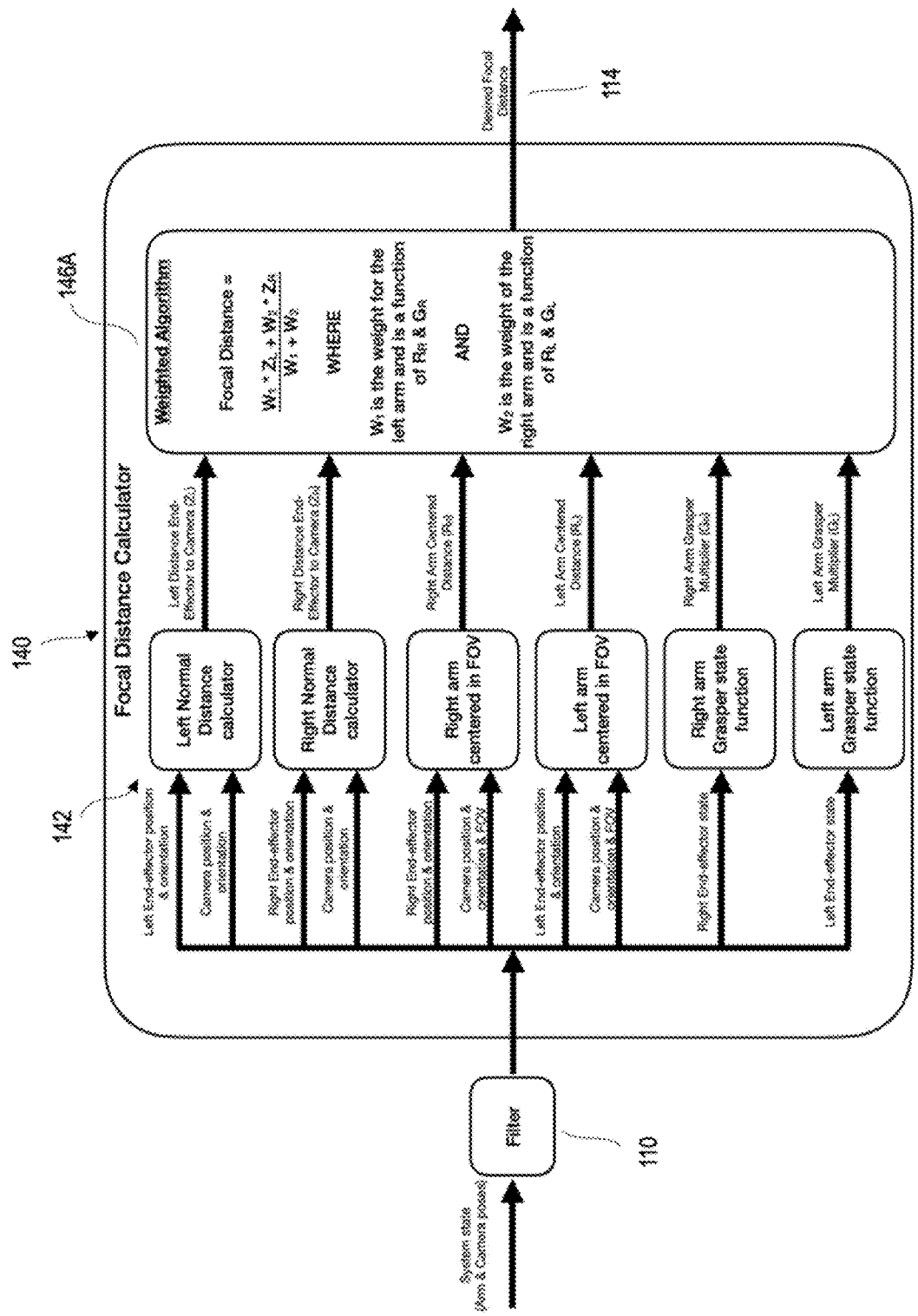
FIG. 6C is a schematic representation illustrating the processing of system state data by a third embodiment of the focal distance calculator unit employed by the surgical robotic system according to the teachings of the present disclosure.

The system parameters may be extracted from the system state data 110 by the data extractor unit 142. An example of this technique is shown for example in FIG. 6C. In the illustrated embodiment, the data extractor unit 142 may include additional calculation units for determining additional system state data 144. The additional system state data 144 is then processed by the weighted algorithm unit 146A. In utilizing how centered an end-effector is in the camera's field of view, the data extractor unit 142 uses the X & Y components of end-effector positions and geometric knowledge of how that relates to the FOV of the camera to compute the distance of a given end-effector to the center of the FOV. In this embodiment, the weight of a given end-effector in the weighted algorithm technique is a function of the distance to the center of the FOV. For example, the more centered the end-effector is, the stronger the weight to that end-effector. When an object is out of view the weight drops. Such a dependency may be desirable because the user is more likely to be focusing on the center of the FOV and thus an end-effector that is closer to the center may be correlated with the user's desire to be focused there.

Figure 7:
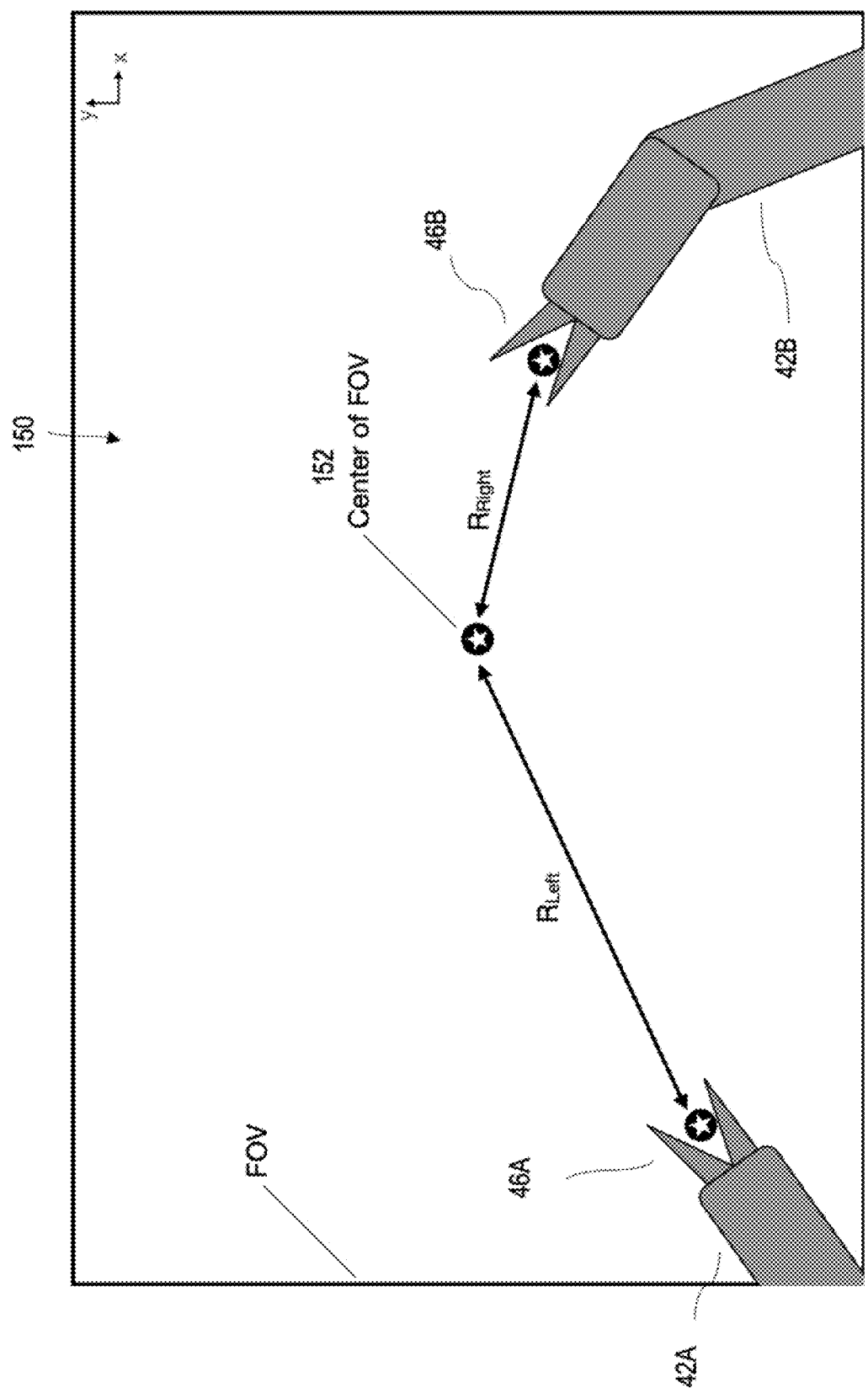
FIG. 7 is a schematic representation of the field of view of the camera assembly unit employed by the surgical robotic system according to the teachings of the present disclosure.

An example of the field of view of the camera assembly is shown for example in FIG. 7. The illustrated field of view 150 has a center 152. The robot arms 42 include the left robot arm 42A that includes the end effector or grasper 46A and the right robot arm 42B with the right end effector or grasper 46B. The system may determine from the image data the right and left robot arm centered distance data $R_{Left}$ and $R_{Right}$.

Figure 8:
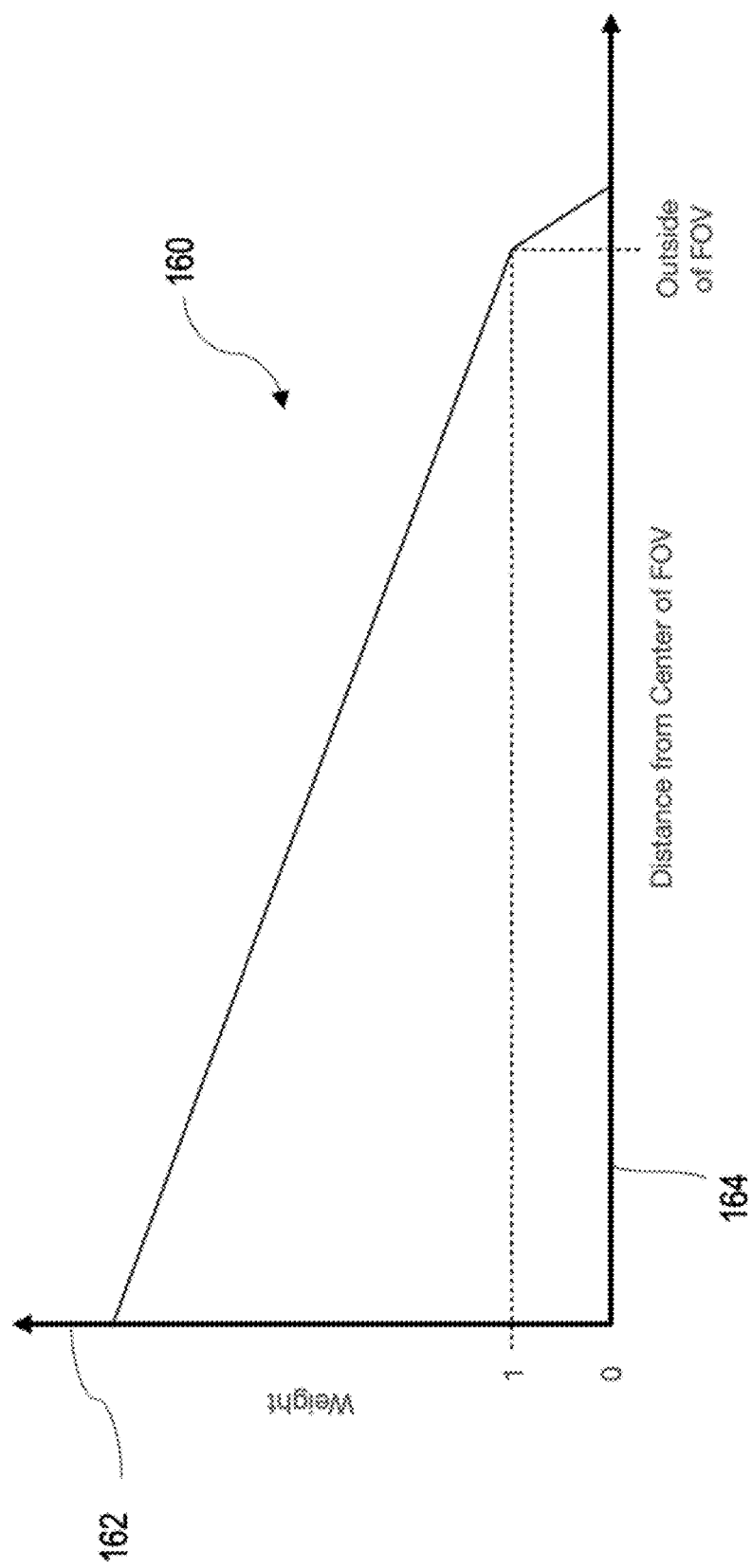
FIG. 8 is a graphical representation of weight graph employed by the surgical robotic system of the present disclosure.

FIG. 8 shows a graph 160 that may be employed by the control unit of the present disclosure. The graph 160 shows weight values along the Y-axis 162 and the distance from the center of the field of view 152 along the X-axis 164. As can be seen, the weights accorded the end effectors decreases as the distance from the center of the FOV increases. In other embodiments, the relationship between the distance from the center of the FOV and any associated weight may take other non-linear forms, such as polynomic, logarithmic, inverse exponential or any other relationship known in the art.

Figure 9:
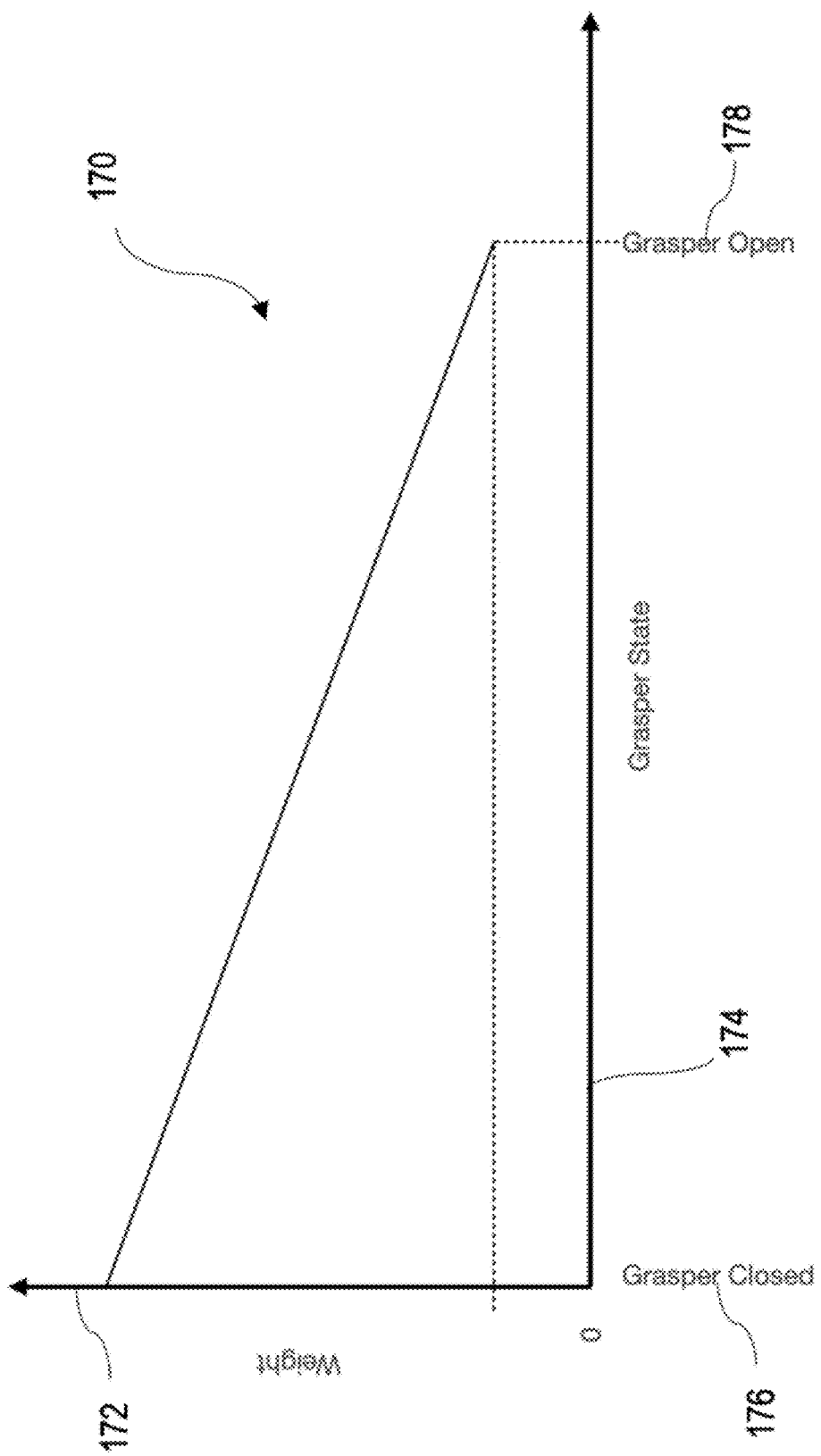
FIG. 9 is a graphical representation of second embodiment of a weight graph employed by the surgical robotic system of the present disclosure.

In still another embodiment, the weight of each robot arm 42A, 42B may be dependent on the state (e.g., opened or closed or in between) of the grasper at the end-effector. For example, if the user is closing the grasper, this may indicate that the user is performing actions that they would like to observe at that end-effector and thus it is desirable for that end-effector to be in focus and thus to be weighted more heavily. FIG. 9 shows a graph 160 that may be employed by the control unit of the present disclosure. The graph 170 shows weight values along the Y-axis 172 and the grasper state along the X-axis 174. The grasper state may vary between a closed state 176 and an opened state 178. As can be seen, the weights accorded the end effectors decreases as the grasper transitions from the closed state to the open state. In other embodiments the relationship between the grasper state and any associated weight may take other non-linear forms, such as polynomic, logarithmic, inverse exponential or any other relationship known in the art.

In other embodiments, a larger weight may be applied to end-effectors that are further away. This biases the output to the further an object is away to allow the background to be more visible more than the foreground. This effectively creates a second order (or higher) dependency on the depth of the end-effector.

Figure 10A:
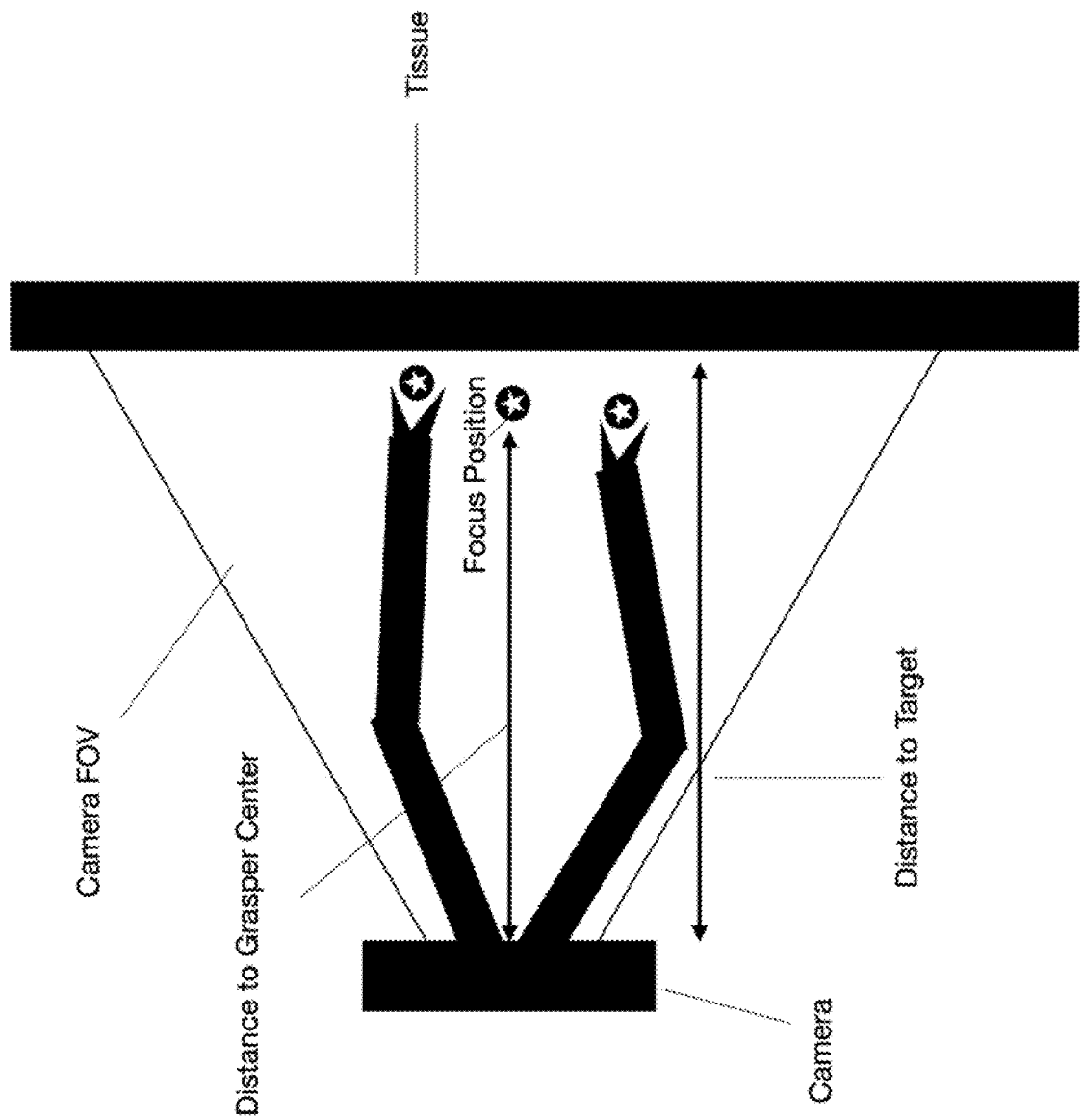
FIGS. 10A-10C are schematic representations of the field of view of the camera assembly unit for limited focal adjustments according to the teachings of the present disclosure.
Figure 10B:
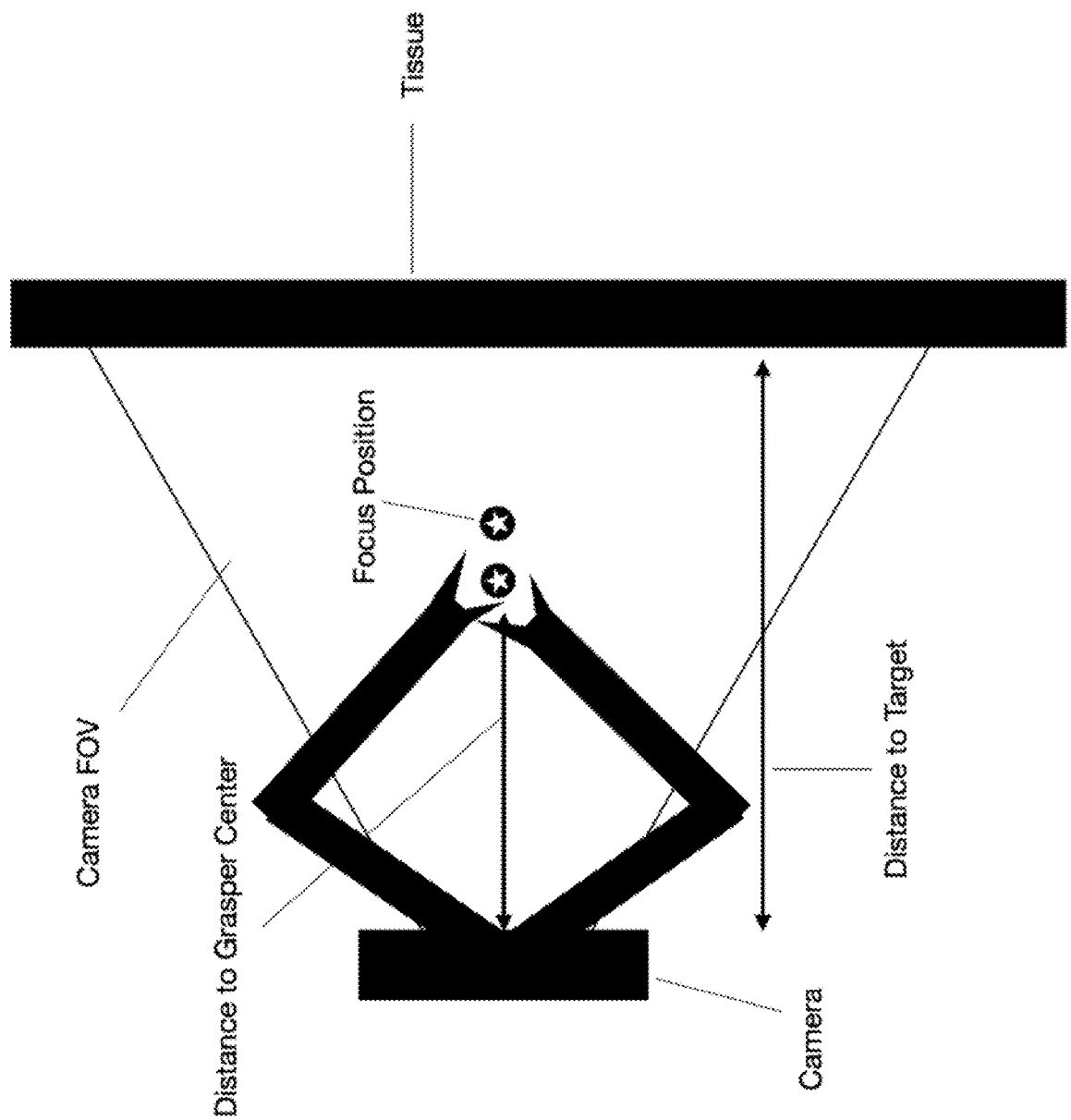
Figure 10C:
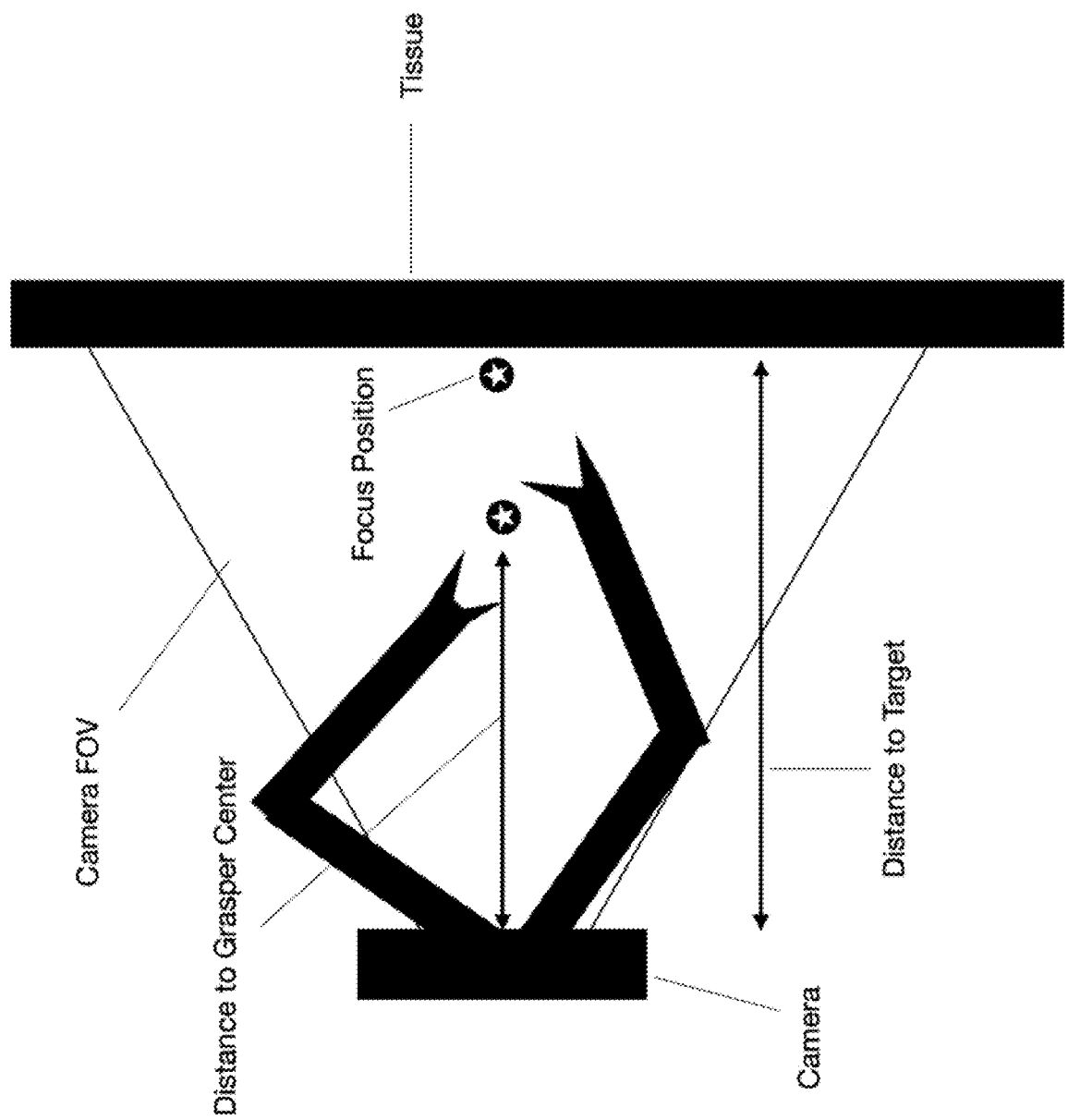

As shown in FIGS. 10A-10C, in certain circumstances it is desirable to limit the automatic focal adjustments. For example, during suturing or other manipulations, it is desirable to reduce the speed of the focus adjustment as the end effectors move toward a patient. The focus adjustment should be rapid as the end effectors of the robotic arms moves away from a patient or a target location (e.g., outward movement) while the adjustment should be slower as the end effectors move towards the patient or the target location. This difference in speed of autofocus provides a stronger performance of autofocus as well as clearer background images. Smaller movements, such as throwing a suture, cause minimal change in the actual set focus position whereas larger movements result in a sharper change. This behavior may be generated using a weight that affects positive movement away more than (stronger than) negative movement. A proportional-integral-derivative (PID) control with highly weighted I/D terms may affect the negative movement in a way that does not provide much change at lower movement changes. FIG. 10A shows an example of such motion in which the focus is slightly in front of the tissue.

As shown in FIG. 10B, the tissue is being manipulated and it is desirable for the focus to remain close to the target. That is, FIG. 10B shows a non-coordinated hand movement or suturing. For example, if a surgeon begins to throw a suture, it is not desirable to immediately change the focus and the focus should remain closer to the tissue than the arm center position. Therefore, a large filter may be applied to the autofocus calculations during rapid movements. FIG. 10C shows an example of longer motions that results in focus position shift towards the task. In this example, the focus may advance faster the closer the end effectors (graspers) are together. The closeness of the end effectors is an indication of coordinated movement.

Still further, the weights $W_1$ and $W_2$ are functions of multiple system parameters and may be simple multiplicative functions of the individual weights of the multiple parameters. An example of a multiplicative weight is as follows:

$$W_1 = wLC * wLG * wLZ$$

where $W_1$ is the overall weight of the left end-effector, wLC is the weight from the distance of the left arm to the center of the FOV, wLG is the weight from the open/closed state of the left grasper, and wLZ is the weight from the depth to the left end-effector.

Figure 11:
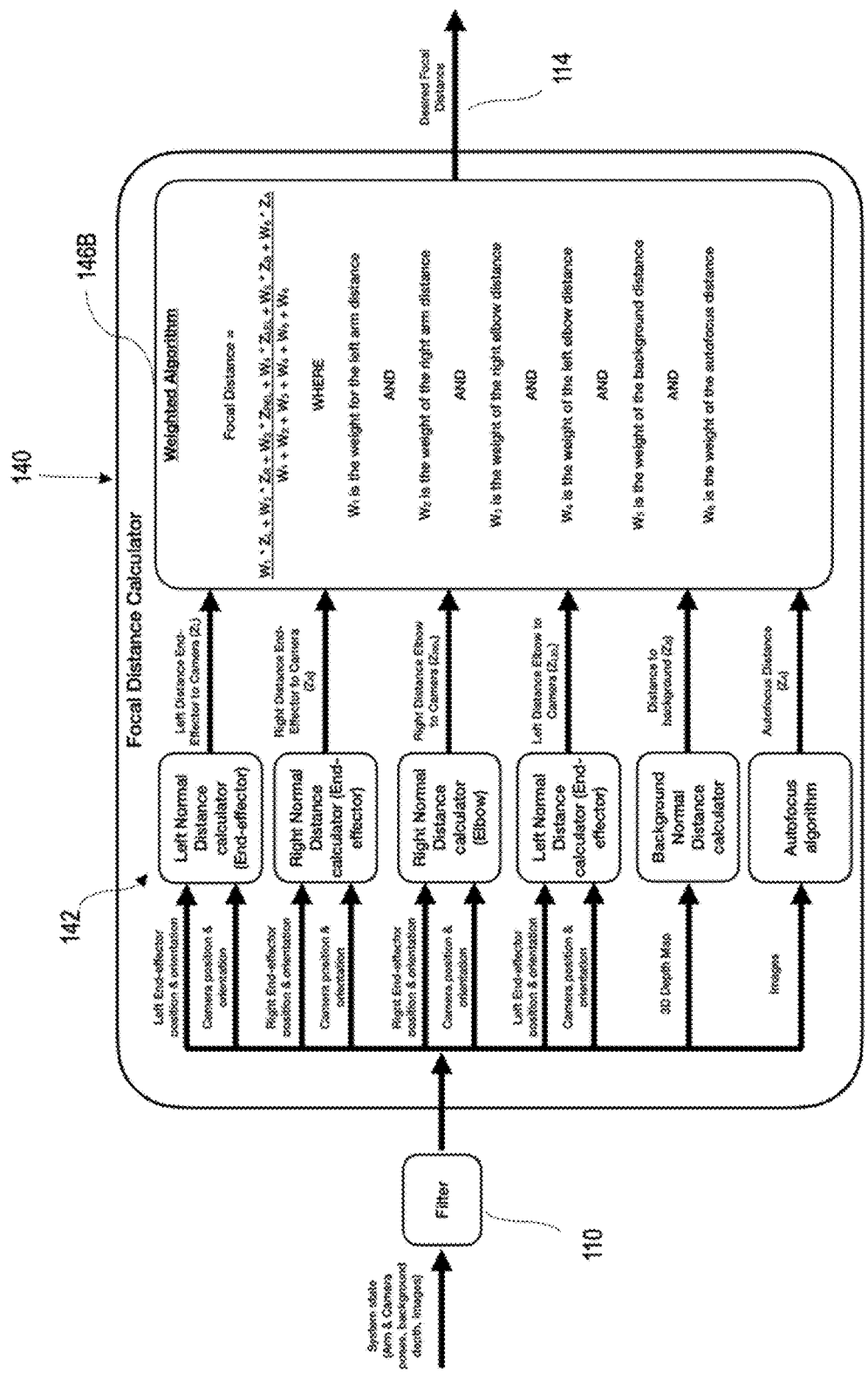
FIG. 11 is a schematic representation illustrating the processing of system state data by a fourth embodiment of the focal distance calculator unit employed by the surgical robotic system according to the teachings of the present disclosure.

In other embodiments, additional distances may be incorporated into the weighted algorithm technique, such as for example elbow distance, background distance and the distance from an autofocus algorithm. An example of a suitable weighted algorithm technique is shown for example in FIG. 11. The illustrated focal distance calculator unit 140 may include the illustrated data extractor unit 142 and the illustrated weighted algorithm unit 146. In the current illustrated example, the elbow joints of the robot arms are additional points of interest that are weighted. According to one practice, the elbow joints may have a weight value associated therewith that is less than the weight value associated with the end-effectors. This is desirable because when looking at the elbow joints alone, with the end-effectors out of the FOV, the output of the weighted algorithm technique may be dominated by the distance the elbow is away from the camera.

Additionally, when the user is viewing the end-effector portions with the elbow joints in view, the weight value associated with the elbow joints may be sufficiently less than the weight values associated with the end-effector, and thus the output may be dominated by the distance of the end-effector. In other embodiments, the focal distance calculator 140 may receive as input the image data from the camera assembly and utilize a PDAF or other autofocus algorithm to calculate the autofocus distance to place the image in focus. This may be particularly useful in cases where other weighted values fall to zero (or to one in some embodiments). In still other embodiments, the input into the weighted algorithm may include three-dimensional depth information calculated from the stereoscopic image data of the cameras to calculate the distance to the background of the image and then use that information as another input in the calculation of the desired focal distance 114. This can bias the desired focal distance 114 to be closer to the background and may be useful to help expand the depth of field by focusing further away.

The field of view may be determined by the optical elements in the cameras. Each camera may also be tested at the factory to make sure that the FOV is within normal ranges (e.g., within the 60601+−15% diagonal of stated value). Further, as the focus changes so does the FOV of the camera. A compensation curve for the FOV changes with respect to the focus may be calculated based on the lens elements.

The focal distance calculator unit 140 thus takes the weights of each position of interest (e.g., elbow joints, graspers, background, and the like) and then multiplies that by the dot product of the position of interest and the camera's pointing vector. In other embodiments, the system may compute a sphere of influence from the camera that provides a weight value based on location in the sphere. The area in view may be assigned to have larger weighted values associated therewith, where the weighted values may peak at the center of the sphere. Since the camera does not generate a spherical window but rather a rectangle, the position is not a pure dot product and thus needs to be weighted based on the axis position. As such, movement along the X-axis of the camera may have a weaker gradient than movement along the Y-axis, since the X-axis has a larger field of view.

It should be noted that in some embodiments, the weighted algorithm may take different forms than the normalized, linear combination described above. The weighted algorithm may also employ any selected type of filter to combine the state data into the desired focal distance, such as for example Kalman filters or even machine learning techniques to help determine the desired focal distance based upon the system state data.

Figure 12:
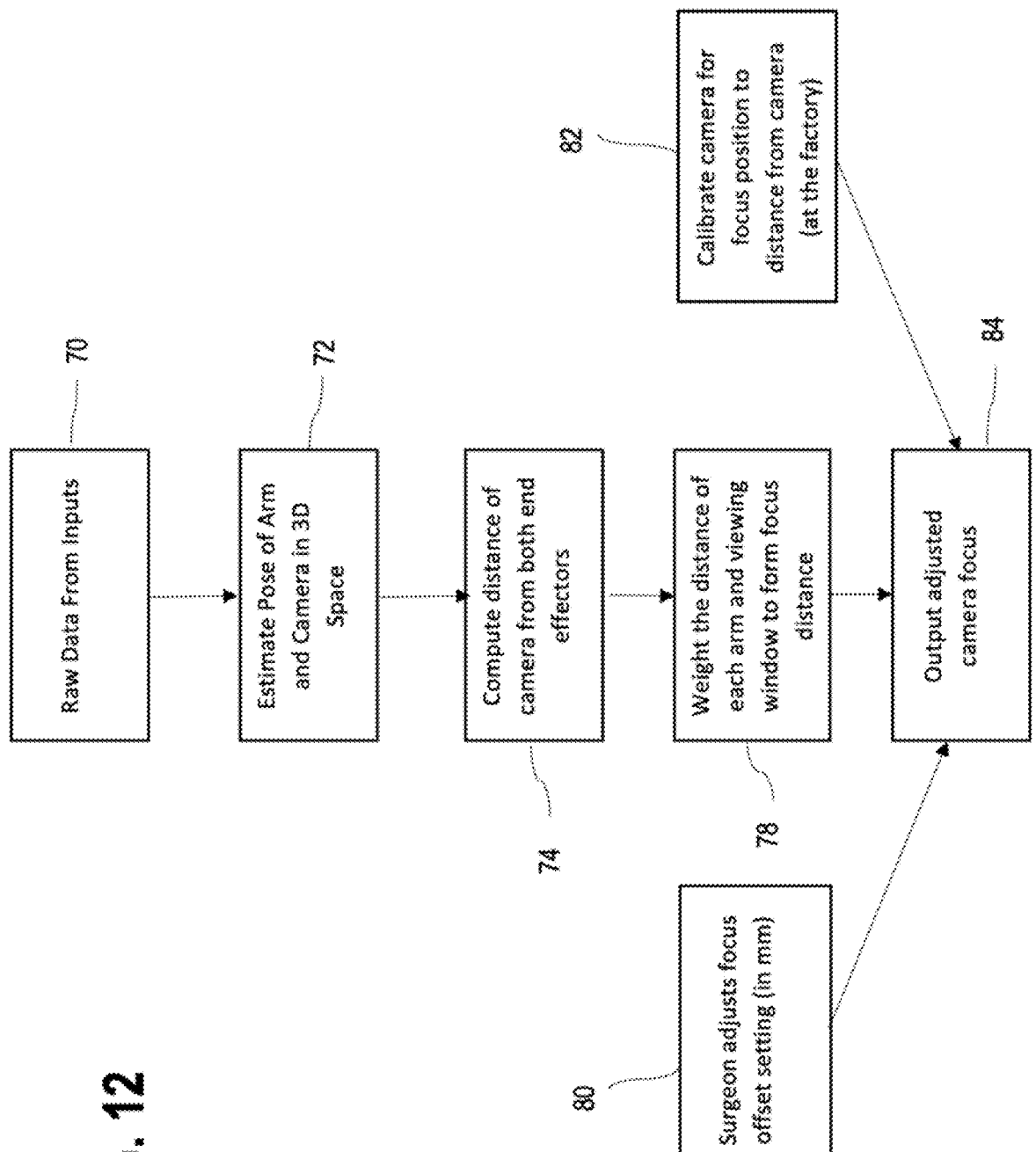
FIG. 12 is a schematic flow chart diagram illustrating the method of automatically focusing the cameras of the camera assembly according to the teachings of the present disclosure.

FIG. 12 is a schematic flow chart diagram illustrating the steps or method employed by the surgical robotic system 10 to automatically focus the cameras of the camera assembly 44 based on one or more system parameters. As shown, the raw positional data of selected components of the surgical robotic system, such as for example sensors (e.g., magnetometers and IUs) and other control inputs, are aggregated and stored in the storage unit 24, step 70. The positional data may be used by the control unit 26 and/or the controller 64 to determine the pose or position of each of the robotic arms 42A, 42B and the camera assembly 44 in a three-dimensional space, step 72.

That is, the controller may calculate the positions of the robotic arms using either a direct measure technique or an indirect measure technique. According to the direct measure technique, the robot arms 42A, 42B and the cameras 60A, 60B each have associated therewith an absolute sensor located in a distalmost joint. The absolute sensor may measure the position and orientation of the distalmost end of the robot arms in six degrees of freedom (e.g., X, Y, Z, Yaw, Pitch, and Roll) relative to a common origin in space. This sensor enables the controller to simply determine the relative positions and orientations of the robot arms and the cameras. Examples of absolute sensors suitable for use with the present disclosure may include alternating magnetic field tracking (such as that incorporated in the technology owned by Polhemus), optical tracking methods and IMUs, as well as others known in the art.

Figure 13:
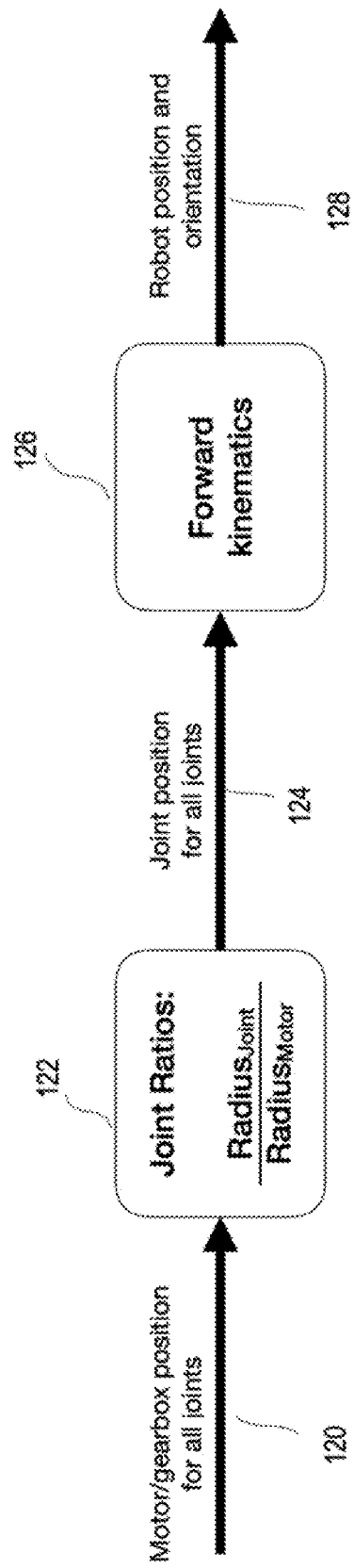
FIGS. 13 and 14 are schematic representations illustrating the processing of system state data, such as motor and joint data, and processed by a forward kinematics unit employed by the surgical robotic system of the present disclosure

According to the indirect measure technique, the pose and position of the robot arms and the cameras is estimated from other parameters known in the system, such as for example by the individual angles of each joint in the arms. Each joint angle is then input into a forward kinematics model of the robot arm to calculate the position and orientation of the distalmost end of the robot or camera in the six degrees of freedom. The robot arm or camera positions may be measured in multiple ways, but all rely on knowing the state of the system. According to one practice, as shown for example in FIG. 13, in a cable driven surgical robot system the controller determines the state of the cables and then uses that information to estimate the location of each joint in the robot arm. As is known, each cable employed in the robot arms changes a particular joint position and hence has a calculable effect on the position of the robot arm and camera assembly.

For example, the system may employ a suitable position sensor, such as a hall effect sensor or potentiometer, positioned on the output of the motor unit 40, that controls the drive cable for a given joint of the robot arm or camera. In this example, the ratio of the motion of the motor to the motion of the robot joint is known and fixed based upon the geometry (e.g., radius) of any motor pulley and drive pulley employed in the joints of the robot arms. Thus, the system may determine that when the motor rotates by X degrees the robot joint moves by Y degrees, where Y=X*R, and where R is the ratio described above. As such, the control unit 26 may determine the motor position 120 for the joints of each of the robot arms. The control unit 26 also determines the joint positions 124 for all joints in the robot arms by using a selected joint ratio 122, which may be defined as the Rj/Rmn, where Rj is the radius of the joint and Rm is the radius of the motor. This calculated joint position 124 and associated motion of the joints may then be input into the forward kinematics model 126 to calculate the position and orientation 128 of the distalmost portion of the robot arms. This method works best when the cable is assumed to be stiff and when friction acting on the cable is low.

Figure 14:
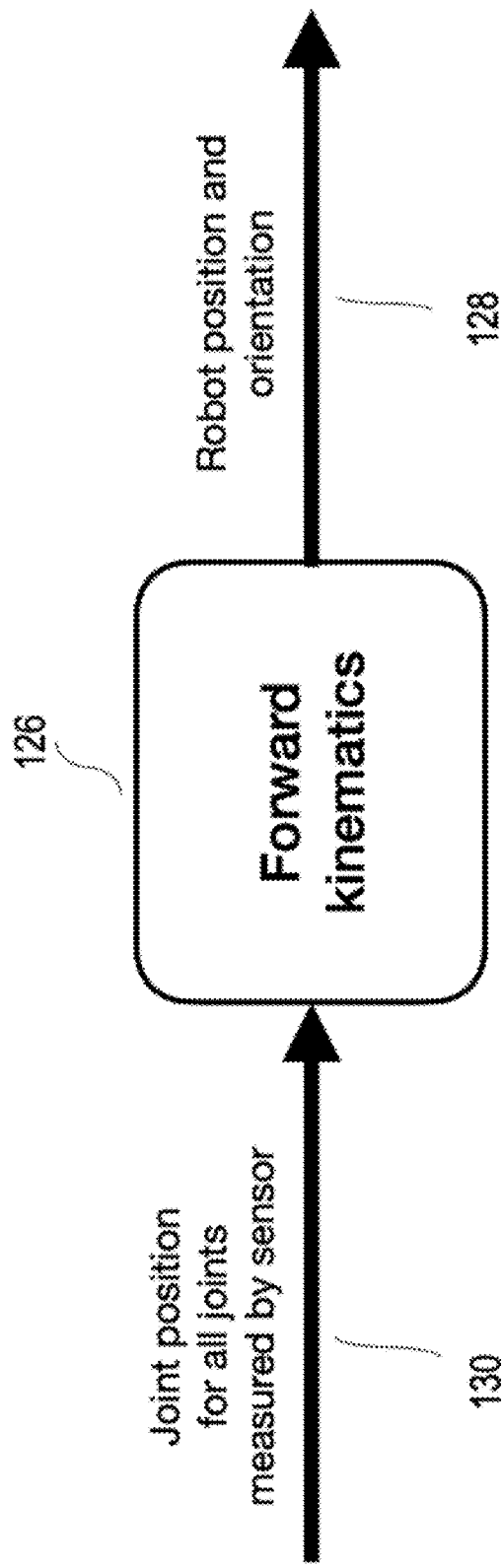

According to one embodiment, as shown in FIG. 14, the angular position of the robot joint may be measured via a sensor that is directly attached at the joint. This may include a hall effect sensor array, potentiometer or other methods known in the art. This type of joint measurement may help with a cable driven system when the cable is not very stiff or the friction acting on the cable is high. In one example, a hall effect sensor array embedded in a joint of the robot arm measures the rotational position of a magnet embedded in an opposite side of the joint, thus enabling direct measurement of the angular position of that joint. As such, the system may, via the sensors, determine the joint position 130 of the robot arms. The joint position 130 may be introduced to a forward kinematics model 126 that processes the joint position data to calculate or determine robot position and orientation 128 of the distalmost portion of the robot arms.

In all indirect measurement methods and techniques, the forward kinematics model 126 of the arm robot and the camera assembly refer to a common origin and coordinate frame. This may be done by utilizing knowledge of the geometric relationships or quantities between the robot arm and camera assembly and may be employed as additional parameters in the forward kinematic model 126. This is not necessary in direct measurement techniques because they are already inherently measuring back to a common origin point.

Regardless of which technique is employed to determine the robot position and orientation, once the position and orientation of the end-effectors of the robot arms and the position and orientation of the cameras are calculated, the distance between the camera and each individual end-effector may be calculated. Further, the indirect and direct measurement techniques may be mixed. For example, the camera assembly may be measured directly, and the robot arms may be measured indirectly or vice versa. In other embodiments, measurement techniques are mixed within one system. For example, a robot may utilize hall effect sensors for one joint and the motor-cable measurement technique for another joint on the same robot.

With the pose or position of each of the robotic arms 42A, 42B and the camera assembly 44 determined by the system 10, the distance of the camera assembly 44 from both of the end effectors 46A, 46B of the robotic arms may be determined or calculated by the control unit 26, step 74. Once the position and orientation of the end-effectors of the robot arms and the position and orientation of the cameras are calculated, the distance between the camera and each individual end-effector may be calculated. This may be calculated in different ways, including employing known mathematical relationships, such as Pythagorean's theorem (in three dimensions), quaternion rotations and translations, vectors and dot products, as well as many other methods known in the art. If the Pythagorean theorem is employed, the theorem determines the X, Y & Z coordinates and then calculates the point to point distance in the following manner:

$$D_{arm\_to\_Camera} = \operatorname{sqrt}[(XEE-XC)2+(YEE-YC)2+(ZEE-ZC)2],$$

where XEE, YEE, and ZEE are the coordinates of the distal end effector of the robot arms and XC, YC, and ZC are the coordinates of the cameras. The vector and dot product method utilizes the dot product of the vector form line of sight of the camera, which may be determined directly from the orientation and geometry of the camera at a given state, and the vector that starts at the camera and ends at the end-effector. This results in the distance that the end-effector is from the camera normal to the line of sight of the camera. This same distance may be calculated by utilizing a quaternion rotation and translation to put the end-effector position and orientation (X, Y, Z, Yaw, Pitch, Roll) in the same coordinate frame as the camera. Once this operation is performed the Z term (the direction normal to the camera) for the end-effector in this new coordinate frame is the distance that the end-effector is from the camera normal to the line of sight of the camera.

Also, the field of view (FOV) is determined by the optical elements in the camera assembly. Each camera 60A, 60B in the camera assembly 44 may be tested at the factory to make sure that the FOV is within an acceptable range. Further, since the FOV changes in direct correlation with changes in the focus, a compensation curve for FOV changes with respect to focus may be calculated based on the optical lens stack employed by the cameras.

The controller 64 may then generate control signals that are received by the autofocus unit 62, and the autofocus unit may automatically adjust the focal point of the cameras 42A, 42B, step 84. Further, the system 10 may also allow the surgeon or user to also manually adjust the focus of the cameras, step 80. Further, the focus curve of the cameras of the camera assembly may be pre-stored in the storage element 24, step 82. The focus curve is an example of how the focus controller converts the desired focal distance 114 into a command that the system may use to achieve that desired focal distance. As such, the desired focal distance 114 may be implemented via a lookup-table or a suitable function of the position of the focus element relative to focal distance. It is known that the lens needs to be calibrated per camera to allow for adjusting the focus as a function of distance of an object.

Figure 15:
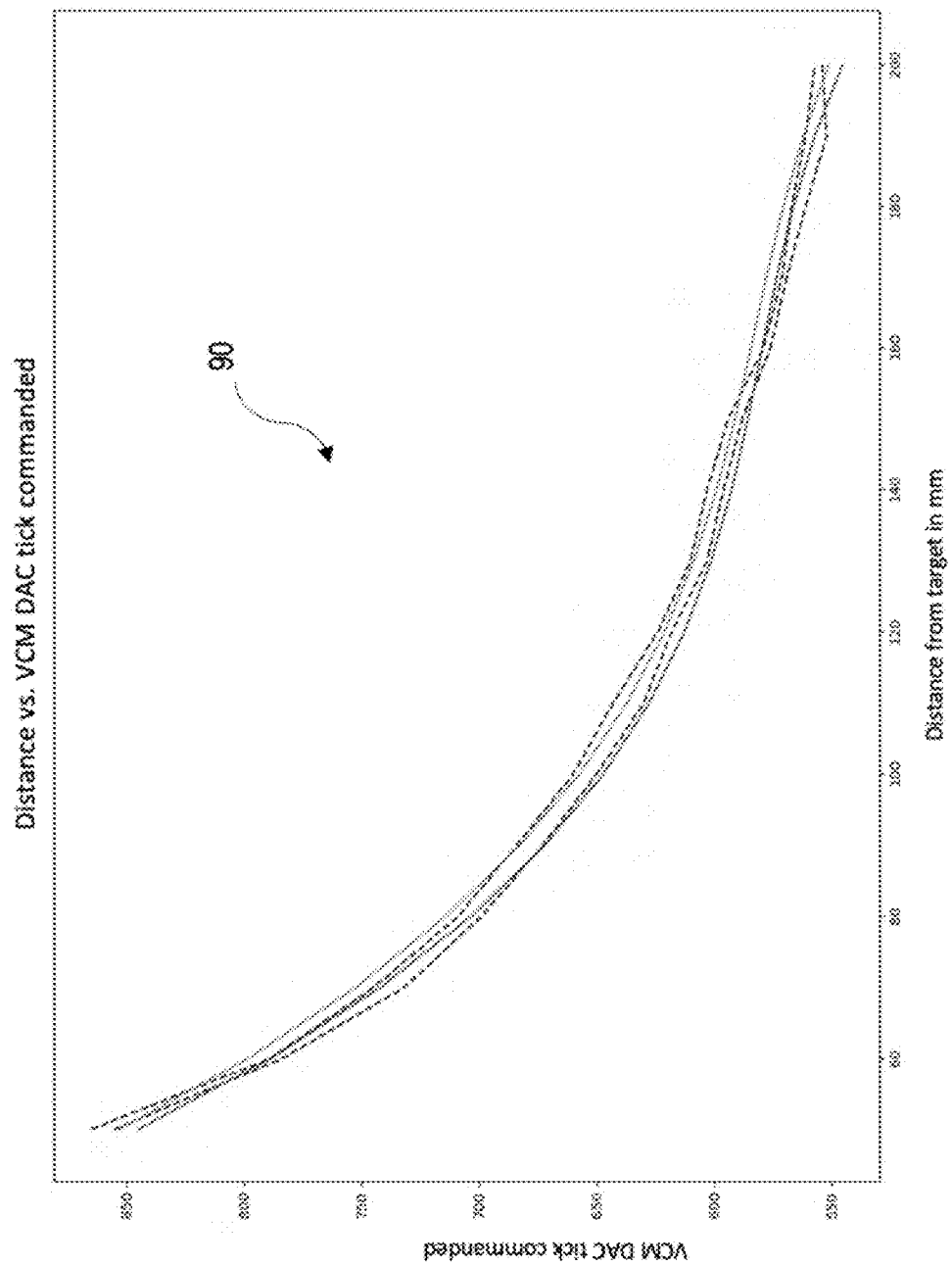
FIG. 15 is an example focus curve that can be prestored and utilized by the controller of the surgical robotic system of the present disclosure.

FIG. 15 is an example of one type of focus curve 90 that may be associated with the cameras 60A, 60B of the surgical robotic system 10. As is illustrated in the focus curve 90, as the distance amplitude correction (DAC) value changes so does the optimal distance to focus changes. As is shown, larger changes are required for targets closer to the camera. This is due to the design of the voice coil module (VCM) where the current commanded has an inverse square relationship to lens movement along with the change required by the VCM becomes smaller the further the distance is away.

Figure 16:
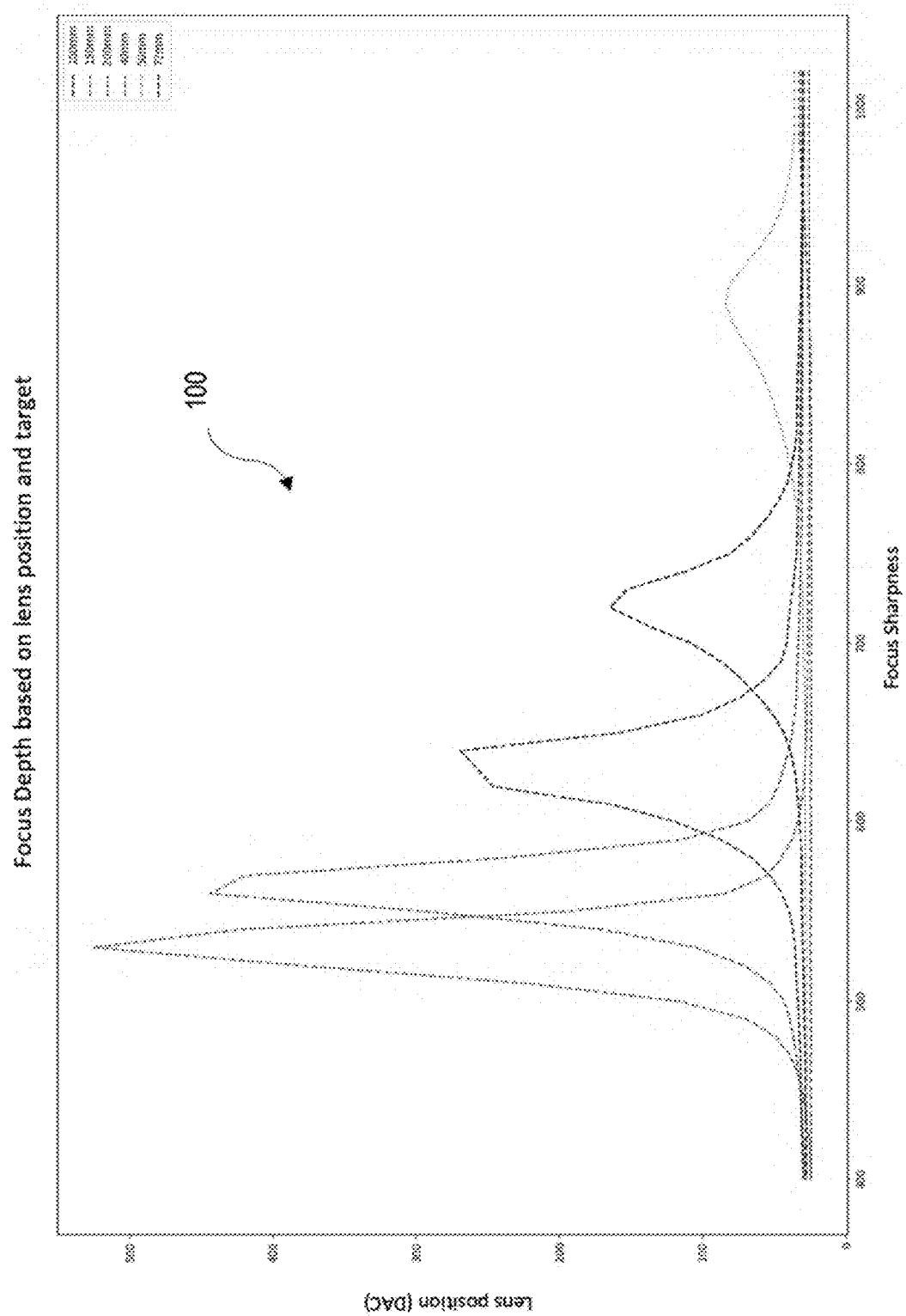
FIG. 16 is an example focus curve having multiple targets at different distances overlaid on each other.

FIG. 16 is a curve that illustrates a defined region of focus of the cameras of the camera assembly 44. The illustrated focus curve 100 includes multiple targets at different distances overlaid on each other. The peak of the illustrated curve 100 over all distances is what is shown above. Note that just because the peak is larger on distances further away does not mean that the image is sharper. Rather, it is the width of the curve relative to that number's distance that matters.

The focus curve of the cameras of the camera assembly 44 may be generated and prestored at the factory in distance space and may be applied and the focus of the cameras adjusted to the location of what the surgeon is looking at using the robotic arms as a minimum position on the depth of the field in the intended scene. As used herein, the term distance space is intended to describe physical distance in space.

The cameras 60A, 60B of the camera assembly 44 may be calibrated and set at the factory prior to being employed in the surgical robotic system 10 of the present disclosure. The camera assembly 44 of the present disclosure is configured to focus on what the surgeon is doing (e.g., the surgical site) while maintaining the largest range of motion possible for the robotic arms. The calibration of the camera assembly 44 may occur at the factory and may include selected tests to determine the resolvability of the cameras 60A, 60B. The calibration of the cameras may occur after final assembly due to the placement of the cameras and the need to register the camera data into selected memory.

During calibration, the output data of each camera may be accumulated and stored in look up tables. A look up table may be associated for example with each camera and associated lens assembly. The process to calibrate the cameras is as follows. The camera may be attached to a motor unit and locked into a selected support fixture that controls the orientation and position of the camera and associated sensor. A one axis stage is used to change the distance of a target from the camera from between about 5 cm and about 20 cm to calibrate the camera at all distances within this range. An interval distance of 10 mm between the cameras in the camera assembly may be used and may be adjusted. The calibration target preferably has sharp edges and is a calibrated resolution target. Each position is sweeped with various VCM currents to get the highest resolution score as determined by the variance of a Laplacian of the center region of the image. The region of interest from the center 50% to the center 10% may be performed in a linear format from distances between about 50 mm and about 200 mm. The output data of the calibration may be employed to form the focus curve 90.

What is claimed is:

1. A surgical robotic system, comprising:
  a plurality of robotic arms each having an end effector at a distal end thereof;
  a camera assembly having at least two cameras and an autofocus unit configured to automatically focus a lens of each of the at least two cameras;
  a sensor unit; and
  a controller configured to calculate a desired focal distance for the camera assembly based on state information including positional information and orientation information of the end effector of each of the plurality of robotic arms received from the sensor unit and a weighted algorithm, each of the plurality of robotic arms is weighted differently in the weighted algorithm.

2. The surgical robotic system of claim 1, wherein:
  the autofocus unit is configured to automatically focus the lens of each of the at least two cameras based on the desired focal distance.

3. The surgical robotic system of claim 1, wherein the state information further includes a distance from each camera to each end effector of the plurality of robotic arms that is within a field of view of a surgeon.

4. The surgical robotic system of claim 1, wherein the state information further includes positional information and orientation information of each camera.

5. The surgical robotic system of claim 1, wherein, based on the calculated desired focal distance, the controller is configured to determine a focus command according to a particular focal depth.

6. The surgical robotic system of claim 5, wherein the controller is configured to transmit the focus command to the autofocus unit and in response, the autofocus unit is configured to adjust a focal point of each camera to focus the lens of each camera.

7. The surgical robotic system of claim 5, wherein the controller is configured to filter the desired focal distance to reduce rapid changes in focal data.

8. The surgical robotic system of claim 7, wherein a strength of a filter for filtering the desired focal distance is varied based on a magnitude of head motion of a surgeon.

9. The surgical robotic system of claim 1, wherein a different desired focal distance is calculated for each of the at least two cameras.

10. The surgical robotic system of claim 1, wherein weights of each robotic arm are functions based on system parameters.

11. The surgical robotic system of claim 10, wherein each robotic arm includes a plurality of joints.

12. The surgical robotic system of claim 11, wherein the plurality of joints includes a shoulder joint, an elbow joint, and a wrist joint.

13. The surgical robotic system of claim 12, wherein the system parameters include a distance from center of each end effector in a field of view of each camera, a state of each end effector, and a position of the elbow joint.

14. The surgical robotic system of claim 1, wherein a focus adjustment speed is increased as each end effector moves outward from a target location.

15. The surgical robotic system of claim 1, wherein a focus adjustment speed is decreased as each end effector moves toward a target location.

16. A robotic subsystem, comprising:
a plurality of robotic arms each having an end effector at a distal end thereof;
a camera assembly including:
at least two cameras;
a controller;
and an autofocus unit configured to automatically focus a lens of each of the at least two cameras,
wherein the controller is configured to calculate a desired focal distance based on state information including positional information and orientation information of the end effector of each of the plurality of robotic arms received from a sensor unit and a weighted algorithm, each of the plurality of robotic arms is weighted differently in the weighted algorithm, and
wherein the autofocus unit is configured to automatically focus the lens of each of the at least two cameras based on the desired focal distance.

17. The robotic subsystem of claim 16, wherein a focus adjustment speed is increased as the robotic arms move outward from a target location and is decreased as the robotic arms move inward toward the target location.

18. The robotic subsystem of claim 16, wherein the state information further includes at least one of a distance from each camera to each end effector of the plurality of robotic arms that is within a field of view of a surgeon and positional and orientation information of the at least two cameras.

* * * * *